United States Patent [19]

Fukami et al.

[11] Patent Number: 5,691,335
[45] Date of Patent: Nov. 25, 1997

[54] IMIDAZOLIDINE DERIVATIVE AND USE THEREOF

[75] Inventors: Harukazu Fukami, Kyoto; Motoo Sumida, Uji; Shinjiro Niwata, Takatsuki; Saki Kakutani; Saitoh Masayuki, both of Ibaraki; Shibata Hiroshi, Takatsuki; Kiso Yoshinobu, Ibaraki, all of Japan

[73] Assignee: Suntory Limited, Osaka, Japan

[21] Appl. No.: 615,277

[22] PCT Filed: Jul. 26, 1995

[86] PCT No.: PCT/JP95/01485

§ 371 Date: Mar. 28, 1996

§ 102(e) Date: Mar. 28, 1996

[87] PCT Pub. No.: WO96/04248

PCT Pub. Date: Feb. 15, 1996

[30] Foreign Application Priority Data

Jul. 29, 1994 [JP] Japan .................. 6-207867
Dec. 7, 1994 [JP] Japan .................. 6-333706

[51] Int. Cl.[6] .................. A61K 31/415; A61K 31/495; C07D 233/80; C07D 233/86
[52] U.S. Cl. .................. 514/235.8; 514/255; 514/314; 514/341; 514/389; 544/139; 544/370; 546/152; 546/274.1; 548/311.1; 548/317.5; 548/318.5; 548/319.1
[58] Field of Search .................. 548/318.5, 319.1, 548/317.5, 311.1; 514/389, 235.8, 255, 314, 341; 544/139, 370; 546/152, 274.1

[56] References Cited

U.S. PATENT DOCUMENTS 3,183,242  5/1965  Dithmar et al. .................. 548/318.5
4,151,290  4/1979  Takayama et al. .................. 548/318.5
4,166,124  8/1979  Wellinga et al. .................. 514/389
4,474,796  10/1984  Kisida et al. .................. 548/318.5

FOREIGN PATENT DOCUMENTS 58-55468  4/1983  Japan .
62-67075  3/1987  Japan .

OTHER PUBLICATIONS

Identification of a Highly Specific Chymase as the Major Angiotensin II–forming Enzyme in the Human Heart, Urata et al, J. Biol. Chem., vol. 265, No. 36, pp. 22348–22357 (1990). (This reference is discussed at p. 4, lines 6–7 of the specification.).

Wellinga et al., J. Agr. Food. Chem., 21(3), 1973, 348–54.

Viski et al., Acta Chim. Hung., 112(3), 1983, 323–34.

Primary Examiner—Floyd D. Higel
Attorney, Agent, or Firm—Oblon, Spivak, McClelland, Maier & Neustadt, P.C.

[57] ABSTRACT

The invention relates to an imidazolidine derivative represented by the following general formula (1):

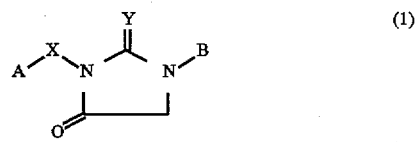

wherein A and B mean individually an aromatic hydrocarbon group which may be substituted by 1–3 substituents selected from halogen atoms, $C_{1-4}$ alkyl groups, $C_{1-4}$ alkoxy groups, $C_{1-4}$ alkylenedioxy groups, a phenoxy group, a nitro group, a cyano group, a phenyl group, $C_{2-5}$ alkanoylamino groups, a carboxyl group which may be esterified with a $C_{1-4}$ alkyl or alkenyl group, carboxyalkyl groups which may be esterified with a $C_{1-4}$ alkyl or alkenyl group, carboxyalkyloxy groups which may be esterified with a $C_{1-4}$ alkyl or alkenyl group, N-alkylpiperazinylcarbonyl groups, N-alkylpiperazinylcarbonylalkyl groups, N-alkylpiperazinylcarbonylalkyloxy groups, and a morpholinocarbonyl group; X denotes a sulfonyl or carbonyl group; and Y stands for an oxygen or sulfur atom, a chymase inhibitor comprising the same as an active ingredient, and a medicine comprising the same as an active ingredient, typified by a prophylactic and therapeutic agent for a disease of the heart or circulatory system, which is caused by the abnormal acceleration of production of angiotensin II.

5 Claims, No Drawings

IMIDAZOLIDINE DERIVATIVE AND USE THEREOF

This application is A 371 PCT/JP 95/01485 filed Jul. 26, 1995.

TECHNICAL FIELD

The present invention relates to an imidazolidine derivative, a chymase inhibitor comprising the same as an active ingredient and a medicine comprising the same as an active ingredient, such as a prophylactic and therapeutic agent for a disease of the cardiac or circulatory system, which is caused by the abnormal acceleration of production of angiotensin II.

BACKGROUND ART

A renin-angiotensin system is one of mechanisms by which the blood pressure of a living body is controlled. Angiotensin I (hereinafter abbreviated as "Ang I") is excised from angiotensinogen biosynthesized in vivo by a renal enzyme renin, and two amino acid residues of its C-terminal are liberated to form angiotensin II (hereinafter abbreviated as "Ang II"). It is considered that this Ang II constricts a peripheral vessel and stimulates a sympathetic nerve, thereby exhibiting a hypertensive effect. Accordingly, Ang II is an important substance for maintaining the blood pressure. It is however considered that the abnormal acceleration of its production may result in an attack of hypertension or heart failure. From such a point of view, attention is paid to the relation between an enzyme [angiotensin converting enzyme (hereinafter abbreviated as "ACE")], which converts Ang I to Ang II, and diseases of the heart or circulatory organs, including hypertension, and various ACE inhibitors have been developed as anti-hypertensive and anti-cardiodysfunctional agents.

Recently, it has also been revealed that Ang II has an action of facilitating cell growth in addition to the actions of constricting the peripheral vessel and stimulating the sympathetic nerve. For example, Naftilan et al. have used cultured cells of a rat vascular smooth muscle to show that Ang II plays an important part in the growth of a vascular smooth muscle [Hypertension, Vol. 13, pp. 706-711 (1989)]. These facts have revealed that Ang II serves as a growth factor for myocardial cells, interstitial cells, angioendothelial cells and vascular smooth muscle cells and so deeply affects the progress of intravascular stenosis attendant on sclerotic vascular lesions, vascular restenosis after the operation of percutaneous transluminal coronary angioplasty (hereinafter abbreviated as "PTCA"), arteriosclerosis, peripheral circulatory failure, diabetic and nondiabetic nephropathy, and a morbid state called the remodeling of ventricular structure after myocardial infarction.

On the basis of these findings, it has been variously attempted to prevent and treat these diseases by suppressing the cell growth-facilitating action of Ang II with an ACE inhibitor. For example, in Europe, the prophylactic effect of an ACE inhibitor, cilazapril on the vascular restenosis after the operation of PTCA has been evaluated by random multifacility collaboration using a placebo as a control. In this clinical study, however, no statistically significant difference has been recognized between cilazapril and the placebo, and so it has been unable to be confirmed that cilazapril has an efficacy in the prevention of vascular restenosis after the operation of PTCA [Circulation, Vol. 86, No. 1, pp. 100-110 (1992)].

The result of this clinical study suggests that an Ang II producing pathway in which no ACE participates exists in the human. In fact, Okunishi et al. have identified another enzyme than ACE, which converts Ang I to Ang II, in canine, simian and human arterial tissues [J. Hypertension, Vol. 2, pp. 277 (1984), and Biochem. Biophys. Res. Commun., Vol. 149, pp. 1186 (1987)]. This enzyme is an enzyme belonging to the serine protease and referred to as chymase, and converts Ang I to Ang II with better efficiency and higher selectivity than ACE. The enzymatic activity of this enzyme is inhibited by chymostatin, but not inhibited by any ACE inhibitor. Namely, it is considered that in the human, two pathways of an ACE pathway inhibited by ACE inhibitors and a chymase pathway not inhibited by any ACE inhibitor exist as pathways in which Ang II is produced, and so in the clinical study described above, a clinical effect could not be sufficiently achieved even when the ACE pathway was blocked by the ACE inhibitor because the chymase pathway has still functioned.

On the other hand, Urata et al. have purified chymase from the human heart and shown that 70 to 80 percent of the amount of Ang II produced in the heart and blood vessel is accounted for by the chymase pathway [J. Biol. Chem., Vol. 265, pp. 22348-22357 (1990)]. Namely, this report suggests that it is important to inhibit chymase rather than ACE for the prophylaxis of and treatment for diseases of the cardiac or circulatory system, which are caused by the abnormal acceleration of production of angiotensin II, and chymase inhibitors can be applied to the diseases of the cardiac or circulatory system.

At present, a trypsin inhibitor derived from soybean and an α-anti-trypsin, which are both proteins, chymostatin, which is a peptide derivative, phenylmethylsulfonyl fluoride, which is an irreversible inhibitor, and the like have been known as chymase inhibitors. It is however practically impossible to clinically apply the trypsin inhibitor derived from soybean and the α-anti-trypsin, which are proteins. Since the peptide linkage of chymostatin is easily decomposed in vivo, it is difficult to put it to practical use. The irreversible inhibitor is considered to be impossible to clinically apply it because of its non-selective activity. Namely, no clinically applicable chymase inhibitor has been found to date. There is thus a demand under the circumstances for development of a clinically applicable chymase inhibitor tied in with the prophylaxis of and treatment for diseases of the cardiac or circulatory system, which are caused by the abnormal acceleration of production of angiotensin II.

DISCLOSURE OF THE INVENTION

In order to solve the problems above, the present inventors have extensively carried out synthesis and development using, as an index, the inhibitory activity against human heart chymase purified according to the process of Urata et al. (see the literature described above). As a result, it has been found that imidazolidine derivatives represented by the general formula (1), which will be described subsequently, inhibit chymase, and further found that these compounds are useful as medicines typified by prophylactic and therapeutic agents for diseases of the cardiac or circulatory system, which are caused by the abnormal acceleration of production of angiotensin II, thus leading to completion of the present invention.

Namely, the present invention provides an imidazolidine derivative represented by the following general formula (1):

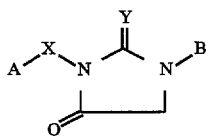

(1)

wherein A and B are identical with or different from each other and mean individually an aromatic hydrocarbon group which may be substituted by 1–3 substituents selected from halogen atoms, alkyl groups having 1–4 carbon atoms, alkoxy groups having 1–4 carbon atoms, alkylenedioxy groups having 1–4 carbon atoms, a phenoxy group, a nitro group, a cyano group, a phenyl group, alkanoylamino groups having 2–5 carbon atoms, a carboxyl group which may be esterified with an alkyl or alkenyl group having 1–4 carbon atoms, carboxyalkyl groups which may be esterified with an alkyl or alkenyl group having 1–4 carbon atoms, carboxyalkyloxy groups which may be esterified with an alkyl or alkenyl group having 1–4 carbon atoms, N-alkylpiperazinylcarbonyl groups, N-alkylpiperazinylcarbonylalkyl groups, N-alkylpiperazinylcarbonylalkyloxy groups, and a morpholinocarbonyl group; X denotes a sulfonyl or carbonyl group; and Y stands for an oxygen or sulfur atom.

The present invention also provides a medicine comprising the imidazolidine derivative (1) as an active ingredient.

The present invention further provides a chymase inhibitor comprising the imidazolidine derivative (1) as an active ingredient.

The present invention still further provides a medicinal composition comprising the imidazolidine derivative (1) and a pharmaceutically permissible carrier.

The present invention yet still further provides use of the imidazolidine derivative (1) for a medicine.

The present invention yet still further provides a method of preventing and treating a disease of the cardiac or circulatory system, which is caused by the abnormal acceleration of production of angiotensin II, comprising administering an effective amount of the imidazolidine derivative (1) to a patient.

BEST MODE FOR CARRYING OUT THE INVENTION

The imidazolidine derivatives according to the present invention are those represented by the general formula (1). In the general formula (1), the aromatic hydrocarbon groups indicated by A and B includes phenyl, naphthyl, indenyl, anthracenyl and phenanthrenyl groups, and the like. Of these, phenyl and naphthyl groups are particularly preferred.

Groups substitutable on the rings of these aromatic hydrocarbon groups include 1–3 substituents selected from halogen atoms, alkyl groups having 1–4 carbon atoms, alkoxy groups having 1–4 carbon atoms, alkylenedioxy groups having 1–4 carbon atoms, a phenoxy group, a nitro group, a cyano group, a phenyl group, alkanoylamino groups having 2–5 carbon atoms, a carboxyl group which may be esterified with an alkyl or alkenyl group having 1–4 carbon atoms, carboxyalkyl groups which may be esterified with an alkyl or alkenyl group having 1–4 carbon atoms, carboxyalkyloxy groups which may be esterified with an alkyl or alkenyl group having 1–4 carbon atoms, N-alkylpiperazinylcarbonyl groups, N-alkylpiperazinylcarbonylalkyl groups, N-alkylpiperazinylcarbonylalkyloxy groups, and a morpholinocarbonyl group. Of these, examples of the halogen atoms include fluorine, chlorine, bromine and iodine atoms. Examples of the alkyl groups having 1–4 carbon atoms include straight-chain alkyl groups such as methyl, ethyl, n-propyl and n-butyl groups, and branched alkyl groups such as isopropyl, sec-butyl and tert-butyl groups. Further, examples of the alkoxy groups having 1–4 carbon atoms include straight-chain alkyloxy groups such as methoxy, ethoxy, n-propyloxy and n-butoxy groups, and branched alkyloxy groups such as isopropyloxy, sec-butoxy and tert-butoxy groups.

The alkylenedioxy groups having 1–4 carbon atoms include methylenedioxy, ethylenedioxy and trimethylenedioxy groups, etc., with the ethylenedioxy group being particularly preferred. The alkanoylamino groups having 2–5 carbon atoms include acetylamino, propionylamino, butyrylamino and pentanoylamino groups, etc., with the acetylamino group being particularly preferred.

Examples of the alkyl groups having 1–4 carbon atoms, with which the above-mentioned carboxyl, carboxyalkyl or carboxyalkyloxy group may be esterified, include straight-chain alkyl groups such as methyl, ethyl, n-propyl and n-butyl groups, and branched alkyl groups such as isopropyl, sec-butyl and tert-butyl groups. The alkenyl groups, with which these groups may be esterified, include vinyl, allyl and 3-butenyl groups, etc. The carboxyalkyl groups are preferably carboxy-$C_{1-4}$-alkyl groups. Specific examples thereof include carboxymethyl, 2-carboxyethyl and 3-carboxypropyl groups. Further, the carboxyalkyloxy groups are preferably carboxy-$C_{1-4}$-alkyloxy groups. Specific examples thereof include carboxymethoxy, 2-carboxyethoxy and 3-carboxypropoxy groups.

Alkyl groups on the nitrogen atoms in the N-alkylpiperazinylcarbonyl groups, N-alkylpiperazinylcarbonylalkyl groups or N-alkylpiperazinylcarbonylalkyloxy groups include alkyl groups having 1–4 carbon atoms. Examples of the alkyl groups having 1–4 carbon atoms include straight-chain alkyl groups such as methyl, ethyl, n-propyl and n-butyl groups, and branched alkyl groups such as isopropyl, sec-butyl and tert-butyl groups. The N-alkylpiperazinylcarbonylalkyl groups are preferably N—$C_{1-4}$-alkylpiperazinylcarbonyl-$C_{1-4}$-alkyl groups. Specific examples thereof include N—$C_{1-4}$-alkylpiperazinylcarbonylmethyl, N—$C_{1-4}$-alkylpiperazinylcarbonylethyl and N—$C_{1-4}$-alkylpiperazinylcarbonylpropyl groups. Further, the N-alkylpiperazinylcarbonylalkyloxy groups are preferably N—$C_{1-4}$-alkylpiperazinylcarbonyl-$C_{1-4}$-alkyloxy groups. Specific examples thereof include N—$C_{1-4}$-alkylpiperazinylcarbonylmethoxy, N—$C_{1-4}$-alkylpiperazinylcarbonylethoxy and N—$C_{1-4}$-alkylpiperazinylcarbonylpropoxy groups.

The aromatic hydrocarbon groups indicated by A and B may have, on their rings, 1–3 substituents selected from the above-mentioned groups. Groups substitutable on the aromatic hydrocarbon group of A are preferably groups selected from the halogen atoms, alkyl groups having 1–4 carbon atoms, alkoxy groups having 1–4 carbon atoms, alkylenedioxy groups having 1–4 carbon atoms, a phenoxy group, nitro group, cyano group, phenyl group, carboxyl group which may be esterified with the alkyl or alkenyl group having 1–4 carbon atoms, carboxyalkyl groups which may be esterified with the alkyl or alkenyl group having 1–4 carbon atoms, carboxyalkyloxy groups which may be esterified with the alkyl or alkenyl group having 1–4 carbon atoms, N-alkylpiperazinylcarbonyl groups, N-alkylpiperazinylcarbonylalkyl groups and N-alkylpiperazinylcarbonylalkyloxy groups. More preferable groups substitutable on the aromatic hydrocarbon group of A include the halogen atoms, alkyl groups having 1–4 carbon atoms, alkoxy groups having 1–4 carbon atoms, ethylenedioxy group, phenoxy group, nitro group, cyano group, phenyl group, carboxyl group which may be esterified with the alkyl group having 1–4 carbon atoms or an allyl group, carboxymethyl group which may be esterified with the alkyl group having 1–4 carbon atoms or an allyl group, carboxymethoxy group which may be esterified with the alkyl group having 1–4 carbon atoms or an allyl group, N-methylpiperazinylcarbonyl group, N-methylpiperazinylcarbonylmethyl group and N-methylpiperazinylcarbonylmethoxy group.

On the other hand, groups substitutable on the aromatic hydrocarbon group of B are preferably groups selected from the halogen atoms, alkyl groups having 1–4 carbon atoms, alkoxy groups having 1–4 carbon atoms, phenoxy group, alkanoylamino groups having 2–5 carbon atoms, carboxyl group which may be esterified with the alkyl or alkenyl group having 1–4 carbon atoms, N-alkylpiperazinylcarbonyl groups and morpholinocarbonyl group. More preferable groups substitutable on the aromatic hydrocarbon group of B include the halogen atoms, alkyl groups having 1–4 carbon atoms, alkoxy groups having 1–4 carbon atoms, phenoxy group, acetylamino group, carboxyl group which may be esterified with the alkyl group having 1–4 carbon atoms, N-methylpiperazinylcarbonyl group and morpholinocarbonyl group.

The imidazolidine derivatives (1) according to the present invention can be prepared, for example, in accordance with the following synthesis process (A) or (B) after protecting their corresponding functional groups with suitable protecting groups routinely used in organic chemical reactions as needed.

Synthesis process (A):

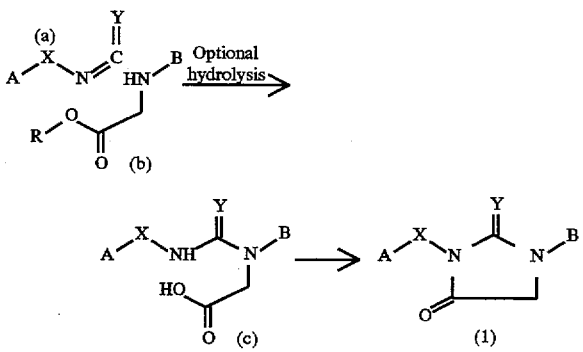

wherein R means a hydrogen atom or a carboxy protecting group, and A, B, X and Y have the same meaning as defined above.

Namely, a (thio)isocyanate derivative (a) is reacted with an N-substituted glycine derivative (b). When R is a carboxy protecting group, the protecting group is then eliminated by hydrolysis to form a compound (c). Thereafter, the compound (c) is subjected to a ring-closing reaction, thereby obtaining an imidazolidine derivative (1) according to the present invention.

The reaction of the (thio)isocyanate derivative (a) with the N-substituted glycine derivative (b) is carried out by stirring the reactants in a temperature range of from room temperature to 100° C. in a solvent such as benzene or tetrahydrofuran in accordance with the conditions of the usual urethanation reaction.

As the carboxy protecting group (R), is preferred an easily leaving group such as a methyl group. As the elimination reaction of the protecting group, is preferred a process in which the protected compound is hydrolyzed with an alkali such as sodium hydroxide.

The ring-closing reaction of the compound (c) is conveniently effected, for example, by reacting a chlorocarbonate with the compound (c) in the presence of a base such as triethylamine.

Synthesis process (B):

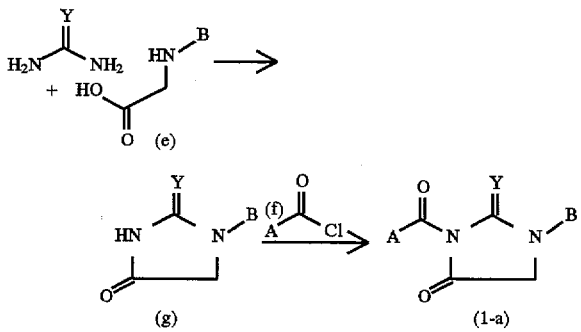

wherein A, B and Y have the same meaning as defined above.

Namely, a (thio)urea (d) and an N-substituted glycine derivative (e) are subjected to deammoniation and dehydration-condensation to form an imidazolidine compound (g). Thereafter, the compound (g) is reacted with an acyl chloride (f), thereby obtaining an imidazolidine derivative (1-a) according to the present invention, in which X is a carbonyl.

The reaction of the (thio)urea (d) with the N-substituted glycine derivative (e) may be conducted in accordance with the conditions of the usual dehydration-condensation reaction, for example, by heating the (thio)urea (d) and N-substituted glycine derivative (e) to 50° C.–200° C. in a solvent or without a solvent, thereby forming the imidazolidine compound (g).

The reaction of the imidazolidine compound (g) with the acyl chloride (f) is conducted in accordance with the conditions of the usual N-acylation reaction, for example, by stirring the reactants in the presence of a base such as pyridine at a temperature ranging from a temperature chilled with ice water to 100° C.

The substituents of the imidazolidine derivatives synthesized in accordance with these processes may be replaced by a method known per se in the art.

As demonstrated by Test Examples which will be described subsequently, the imidazolidine derivatives (1) according to the present invention have excellent inhibitory activities against chymase as well as cathepsin G and chymotrypsin which are kinds of serine protease.

Okunishi et al. [Hideki Okunishi, Naotaka Shioda, Shinji Takai and Mizuo Miyazaki, "Ensho(Inflammation)", Vol. 14, No. 3, pp. 193–197 (1994)] used, as models of balloon injury of the common carotid artery, dogs having the same Ang II producing pathway as the human to consider the role of chymase in the restenosis after PTCA. This paper reported that when balloon injury is inflicted on the common carotid artery of a beagle, hypertrophy occurs in the artery on the injured side, and so ACE and chymase on the injured artery side increase to 4.6 times and 22 times, respectively, at the enzymatic activity level, and also to 4.8 times and 3.4 times, respectively, at the mRNA level as compared with the artery on the control side. It was also described that even in the vascular histological aspect, the Ang II concentration on the injured side increases to about twice the control side.

From these experimental facts, Okunishi et al. considered that when physical injury by a balloon catheter is inflicted on the vascular wall, gene expression in both chymase and ACE rises in response to such infliction, and so their enzymatic activities increase, and concluded that the fact that the enzymatic activity of chymase increases about 5 times as much as that of ACE though ACE rather increases than chymase at the mRNA level indicates that chymase plays an important part in the restenosis after PTCA.

From this report, it is considered that topical increase in the production of Ang II at the injured site, in which chymase participates, is tied, through the growth factor-like activity of Ang II, with the wandering of the smooth muscle into the tunica intima, its growth in the tunica intima, acceleration of extracellular substrate production and the like, and consequently causes the restenosis. The imidazolidine derivatives according to the present invention inhibit human heart chymase as demonstrated by the Test Example which will be described subsequently. This strongly suggests that the compounds according to the present invention suppress the excess production of Ang II through the inhibition of chymase activity, and are hence useful for the prophylaxis of and treatment for diseases of the cardiac or circulatory system, which are caused by the abnormal acceleration of production of Ang II.

Examples of such diseases include heart failure, cardiac hypertrophy, congestive cardiopathy, hypertension, arteriosclerosis, peripheral circulatory failure, vascular restenosis after the operation of PTCA, and diabetic or non-diabetic nephropathy. Since these diseases are said to be caused by the hypertrophy of the heart or tunica intima induced by the growth factor-like activity of Ang II, the imidazolidine derivatives according to the present invention are useful for the prophylaxis of and treatment for these diseases of the cardiac or circulatory system because they inhibit the chymase activity.

When the imidazolidine derivatives according to the present invention are used as a medicine, it is only necessary to use them as a composition in a preparation form according to its manner of administration in accordance with a method known per se in the art by formulating one or more of the imidazolidine derivatives and optionally incorporating a pharmaceutically permissible carrier. Examples of preparation forms for oral administration include capsules, tablets, granules, powders, syrups and dry syrups, while examples of preparation forms for parenteral administration include injections, and besides suppositories such as rectal suppositories and vaginal suppositories, transnasal preparations such as sprays, ointments, and percutaneous preparations such as tapes for percutaneous absorption. In order to enhance the effects of the active ingredients according to the present invention, the imidazolidine derivatives may also be used in combination with ACE inhibitors such as alacepril, captopril and cilazapril, which are being clinically applied.

Clinical dose of the compound according to the present invention varies according to the diseased condition, degree of seriousness, age, presence of a complication, and the like of the patient to be dosed, and also its preparation form. However, in the case of oral administration, it may be dosed in an amount of generally 1–1,000 mg, preferably 1–500 mg, more preferably 5–100 mg per day for an adult. In the case of parenteral administration, it may be dosed in an amount ranging from a tenth to a half of the amount dosed in the case of the oral administration. These doses may be suitably increased or decreased according to the age, diseased condition and the like of the patient to be dosed.

The toxicity of the compounds according to the present invention is low. For example, the acute toxicity values ($LD_{50}$) of compounds of Examples 1 and 2, which will be described subsequently, upon elapsed time of 24 hours after oral administration to male mice aged 5 weeks were not lower than 1 g/kg. This value is at least 50 times of the clinical dose envisaged. Therefore, these compounds are judged to be high in safety.

EXAMPLES

The present invention will hereinafter be described more specifically on the basis of the following examples. However, it goes without saying that the scope of this invention is not limited to these examples.

Example 1

Synthesis of 3-(4-chlorobenzenesulfonyl)-1-(4-chlorophenyl)imidazolidin-2, 4-dione (Compound 1):

Three grams (15 mmol) of methyl 4-chlorophenylaminoacetate were dissolved in 40 ml of benzene, and 2.2 ml (15 mmol) of 4-chlorobenzenesulfonyl isocyanate were added to the resultant solution, followed by stirring for 1 hour. Crystals formed were collected by filtration to obtain N-(4-chlorobenzenesulfonyl)-N'-(4-chlorophenyl)-N'-methoxycarbonylmethylurea (6.1 g) as white crystals.

The thus-obtained urea derivative in an amount of 2.6 g (6.2 mmol) was dissolved in 50 ml of a liquid mixture of methanol/1N NaOH (1/1), and the solution was stirred for 5 hours. The liquid reaction mixture was weakly acidified and then subjected to extraction with ethyl acetate. The organic layer was washed with water, dried over anhydrous magnesium sulfate and then concentrated under reduced pressure. The resultant residue was subjected to crystallization from n-hexane/ethyl acetate, thereby obtaining N-(4-chlorobenzene-sulfonyl)-N'-(4-chlorophenyl)-N'-carboxymethyl-urea (2.2 g) as white crystals.

The thus-obtained carboxylic acid derivative (2.2 g, 5.5 mmol) was dissolved in anhydrous tetrahydrofuran (50 ml), and 2 ml (15.5 mmol) of triethylamine were added to the resultant solution, followed by cooling to 0° C. To the cooled mixture, 0.66 ml (6.9 mmol) of ethyl chlorocarbonate was added, and agitation was conducted for 1 hour at that temperature. Thereafter, the temperature of the mixture was raised to room temperature and stirred for 2 hours. Saturated saline and ethyl acetate were added to the liquid reaction mixture, and the organic layer was washed with saturated saline, dried over anhydrous magnesium sulfate and then concentrated under reduced pressure. The resultant residue was subjected to crystallization from n-hexane/ethyl acetate, thereby obtaining 1.0 g of the title compound as colorless crystals. Besides, the filtrate was concentrated, and the resultant residue was purified by chromatography on silica gel (eluent: n-hexane/ethyl acetate) to obtain 300 mg of the title compound. The total amount of the title compound obtained was 1.3 g (yield: 59.2%).

Appearance: colorless crystals. Melting point: 239°–240° C. PMR (δ ppm, DMSO-$d_6$): 4.49(s,2H), 7.4–8.1(m,8H).

Example 2

Synthesis of 1-phenyl-3-(2-toluenesulfonyl)-imidazolidin-2, 4-dione (Compound 2):

In a similar manner to Example 1, 280 mg (yield: 18.4%) of the title compound were obtained from 1.6 g (4.6 mmol) of N-(2-toluenesulfonyl)-N'-phenyl-N'-carboxymethyl-urea obtained from methyl phenylaminoacetate and 2-toluenesulfonyl isocyanate.

Example 3

Synthesis of 3-benzenesulfonyl-1-phenyl-imidazolidin-2,4dione (Compound 3):

In a similar manner to Example 1, 520 mg (yield: 36.6%) of the title compound were obtained from 1.5 g (4.5 mmol) of N-(benzenesulfonyl)-N'-phenyl-N'-carboxymethylurea obtained from methyl phenylaminoacetate and benzenesulfonyl isocyanate in a similar manner to Example 1.

Appearance: colorless crystals. Melting point: 212.5°–214° C. PMR ($\delta$ ppm, DMSO-$d_6$): 4.53(s,2H), 7.1–8.1(m,10H).

Example 4

Synthesis of 3(4-chlorobenzenesulfonyl)-1- phenyl-imidazolidin-2,4-dione (Compound 4):

In a similar manner to Example 1, 2.3 g (yield: 81.0%) of the title compound were obtained from 3.0 g (8.6 mmol) of N-(4-chlorobenzenesulfonyl)-N'-phenyl-N'-carboxymethylurea obtained from methyl phenylaminoacetate and 4-chlorobenzenesulfonyl isocyanate in a similar manner to Example 1.

Appearance: colorless crystals. Melting point: 188°–192° C. PMR ($\delta$ ppm, CDCl$_3$): 4.27(s,2H), 7.2–8.2(m,9H).

Example 5

Synthesis of 1-phenyl-3-(4-toluenesulfonyl)-imidazolidin-2,4-dione (Compound 5):

In a similar manner to Example 1, 0.6 g (yield: 31.9%) of the title compound was obtained from 2.0 g (5.7 mmol) of N-(4-toluenesulfonyl)-N'-phenyl-N'-carboxymethylurea obtained from methyl phenylaminoacetate and 4-toluenesulfonyl isocyanate in a similar manner to Example 1.

Appearance: colorless crystals. Melting point: 204°–206° C. PMR ($\delta$ ppm, CDCl$_3$): 2.42(s,3H), 4.25(s,2H), 7.2–8.2 (m,9H).

Example 6

Synthesis of 3-(2-chlorobenzenesulfonyl)-1-phenylimidazolidin-2,4-dione (Compound 6):

In a similar manner to Example 1, 760 mg (yield: 27.7%) of the title compound were obtained from 1.4 g (7.82 mmol) of methyl phenylaminoacetate and 1.7 g (7.82 mmol) of 2-chlorobenzenesulfonyl isocyanate.

Appearance: colorless crystals. Melting point: 217°–220° C. PMR ($\delta$ ppm, DMSO-$d_6$): 4.70(s,2H), 7.0–8.2(m,9H).

Example 7

Synthesis of 1-(4-chlorophenyl)-3-(2,4-difluorobenzonyl) imidazolidin-2,4-dione (Compound 7):

In a similar manner to Example 1, 320 mg (yield: 65.6%) of the title compound were obtained from 0.5 g (1.4 mmol) of N-(2,6-difluorobenzoyl)-N'-(4-chlorophenyl)-N,-carboxymethylurea obtained from methyl 4-chlorophenylaminoacetate and 2,6-difluorobenzoyl isocyanate in a similar manner to Example 1.

Appearance: colorless crystals. Melting point: 197°–199.5° C. PMR ($\delta$ ppm, DMSO-$d_6$): 4.65(s,2H), 7.2–7.8(m,7H).

Example 8

Synthesis of 3(4-chlorobenzoyl)-1phenyl-imidazolidin-2,4-dione (Compound 8):

In accordance with the synthesis process (B), 500 mg (2.84 mmol) of 1-phenyl-imidazolidin-2,4-dione were dissolved in 20 ml of pyridine. To the solution, 500 mg (2.86 mmol) of p-chlorobenzoyl chloride were added dropwise while chilling with ice water. The resultant mixture was stirred at 0°–5° C. for 2 hours, and dilute hydrochloric acid was then added to the reaction mixture. Crystals deposited were collected by filtration by means of suction. These crude crystals were recrystallized from n-hexane/ethyl acetate, thereby obtaining 220 mg (yield: 25%) of the title compound.

Appearance: colorless crystals. Melting point: 182°–183.5° C. PMR ($\delta$ ppm, DMSO-$d_6$): 4.63(s,2H), 7.1–8.1(m,9H).

Example 9

Synthesis of 3-benzoyl-1-phenyl-imidazolidin-2,4-dione (Compound 9):

In a similar manner to Example 1, 710 mg (yield: 75.6%) of the title compound were obtained from 1.0 g (3.4 mmol) of N-benzoyl-N'-phenyl-N'-carboxymethylurea obtained from methyl phenylaminoacetate and benzoyl isocyanate in a similar manner to Example 1.

Appearance: colorless crystals. Melting point: 188°–192° C. PMR ($\delta$ ppm, DMSO-$d_6$): 4.66(s,2H), 7.1–8.1(m,10H).

Example 10

Synthesis of 3-(2-chlorobenzoyl)-1-phenyl-imidazolidin-2,4-dione (Compound 10):

In a similar manner to Example 8, 560 mg (3.18 mmol) of 1-phenyl-imidazolidin-2,4-dione were reacted with 560 mg (3.22 mmol) of 2-chlorobenzoyl chloride. After completion of the reaction, pyridine was distilled off under reduced pressure, and the resultant residue was subjected to extraction with ethyl acetate. The organic layer was washed with dilute hydrochloric acid and with saturated saline. The thus-washed organic layer was dried over anhydrous magnesium sulfate, and the solvent was then distilled off. The resultant residue was purified by column chromatography on silica gel (developing solvent: methylene chloride) and subjected to crystallization from n-hexane/ethyl acetate to obtain 130 mg (yield: 12.9%) of the title compound.

Appearance: colorless crystals. Melting point: 184°–185° C. PMR ($\delta$ ppm, CDCl$_3$): 4.45(s,2H), 7.2–7.7(m,9H).

Example 11

Synthesis of 3-(3,4-dichlorobenzoyl)-1-phenyl-imidazolidin-2,4-dione (Compound 11):

In a similar manner to Example 8, 1.5 g (yield: 82.0%) of the title compound were obtained from 930 mg (5.28 mmol) of 1-phenyl-imidazolidin-2,4-dione and 1.1 g (5.28 mmol) of 3,4-dichlorobenzoyl chloride.

Appearance: colorless crystals. Melting point: 202°–203° C. PMR ($\delta$ ppm, DMSO-$d_6$): 4.62(s,2H), 7.1–8.4(m,8H).

Example 12

Synthesis of 1-phenyl-3-(4meyhoxybenzoyl)-imidazolidin-2,4-dione (Compound 12):

In a similar manner to Example 8, 760 mg (yield: 86.3%) of the title compound were obtained from 510 mg (2.90 mmol) of 1-phenyl-imidazolidin-2,4-dione and 500 mg (2.93 mmol) of 4-methoxybenzoyl chloride.

Appearance: colorless crystals. Melting point: 161°–163° C. PMR (δ ppm, DMSO-d$_6$): 3.89(s,3H), 4.66(s,2H), 7.0–8.1(m,9H).

Example 13

Synthesis of 1-phenyl-3-(3-methoxybenzoyl)-imidazolidin-2,4-dione (Compound 13):

In a similar manner to Example 8, 580 mg (3.30 mmol) of 1-phenyl-imidazolidin-2,4-dione were reacted with 560 mg (3.29 mmol) of 3-methoxybenzoyl chloride. After completion of the reaction, pyridine was distilled off under reduced pressure, and the resultant residue was subjected to extraction with ethyl acetate. The organic layer was washed with dilute hydrochloric acid and with saturated saline. The thus-washed organic layer was dried over anhydrous magnesium sulfate, and the solvent was then distilled off. The resultant residue was purified by column chromatography on silica gel (developing solvent: n-hexane/ethyl acetate) and subjected to crystallization from n-hexane/ethyl acetate to obtain 90 mg (yield: 10.2%) of the title compound.

Appearance: colorless crystals. Melting point: 161°–162° C. PMR (δ ppm, DMSO-d$_6$): 3.83(s,3H), 4.64(s,2H), 7.1–7.7(m,9H).

Example 14

Synthesis of 3-(2,6-dimethylbenzoyl)-1-phenyl-imidazolidin-2,4-dione (Compound 14):

In 30 ml of pyridine, were dissolved 1.1 g (6.25 mmol) of 1-phenyl-imidazolidin-2,4-dione and 1.12 g (6.65 mmol) of 2,6-dimethylbenzoyl chloride to conduct a reaction at 60° C. for 3 hours. After completion of the reaction, pyridine was distilled off under reduced pressure, and the resultant residue was subjected to extraction with ethyl acetate. The organic layer was washed with dilute hydrochloric acid and with saturated saline. The thus-washed organic layer was then dried over anhydrous magnesium sulfate, and the solvent was distilled off. The resultant residue was purified by column chromatography on silica gel (developing solvent: n-hexane/ ethyl acetate) and subjected to crystallization from n-hexane/ethyl acetate to obtain 122 mg (yield: 5.8%) of the title compound.

Appearance: colorless crystals. Melting point: 135°–137° C. PMR (δ ppm, CDCl$_3$): 2.33(s,6H), 4.40(s,2H), 7.0–7.6 (m,8H).

Example 15

Synthesis of 3-(4-phenylbenzoyl)-1-phenyl-imidazolidin-2,4-dione (Compound 15):

In a similar manner to Example 8, 530 mg (3.00 mmol) of 1-phenyl-imidazolidin-2,4-dione were reacted with 650 mg (3.00 mmol) of 4-phenylbenzoyl chloride. After completion of the reaction, pyridine was distilled off under reduced pressure, and the resultant residue was subjected to extraction with ethyl acetate. The organic layer was washed with dilute hydrochloric acid and with saturated saline. The thus-washed organic layer was dried over anhydrous magnesium sulfate, and the solvent was then distilled off. The resultant residue was purified by column chromatography on silica gel (developing solvent: n-hexane/ethyl acetate) and subjected to crystallization from n-hexane/ethyl acetate to obtain 100 mg (yield: 9.9%) of the title compound.

Appearance: colorless crystals. Melting point: 196°–198° C. PMR (δ ppm, CDCl$_3$): 4.52(s,2H), 7.2–8.2(m,14H).

Example 16

Synthesis of 3-benzoyl-1-phenyl-imidazolidin-4-one-2-dione (Compound 16):

In a similar manner to Example 1, 1.8 g of N-benzenesulfonyl-N'-phenyl-N'-ethoxycarbonylmethylthiourea were obtained from 1.0 g (5.59 mmol) of ethyl phenylaminoacetate and 960 mg (5.89 mmol) of benzenesulfonyl isothiocyanate. From 1.6 g (4.68 mmol) of the thus-obtained thiourea derivative, 180 mg (yield: 13.0%) of the title compound were obtained in a similar manner to Example 1.

Appearance: colorless crystals. Melting point: 172°–174° C. PMR (δ ppm, CDCl$_3$): 4.66(s,2H), 7.2–8.1(m,10H).

Example 17

Synthesis of 3-(3-phenoxybenzoyl)-1phenyl-imidazolidin-2,4-dione (Compound 17):

In a similar manner to Example 8, 500 mg (2.80 mmol) of 1-phenyl-imidazolidin-2,4-dione were reacted with 600 mg (2.80 mmol) of 3-phenoxybenzoyl chloride. After completion of the reaction, pyridine was distilled off under reduced pressure, and the resultant residue was subjected to extraction with ethyl acetate. The organic layer was washed with dilute hydrochloric acid and with saturated saline. The thus-washed organic layer was dried over anhydrous magnesium sulfate, and the solvent was then distilled off. The resultant residue was subjected to crystallization from n-hexane/ethyl acetate to obtain 780 mg (yield: 69.9%) of the title compound.

Appearance: colorless crystals. Melting point: 157°–158° C. PMR (δ ppm, CDCl$_3$): 4.62(s,2H), 7.0–7.9(m,14H).

Example 18

Synthesis of 3-(2-phenoxybenzoyl)-1phenyl-imidazolidin-2,4-dione (Compound 18):

In a similar manner to Example 8, 500 mg (2.80 mmol) of 1-phenyl-imidazolidin-2,4-dione were reacted with 700 mg (3.00 mmol) of 2-phenoxybenzoyl chloride. After completion of the reaction, pyridine was distilled off under reduced pressure, and the resultant residue was subjected to extraction with ethyl acetate. The organic layer was washed with dilute hydrochloric acid and with saturated saline. The thus-washed organic layer was dried over anhydrous magnesium sulfate, and the solvent was then distilled off. The resultant residue was purified by column chromatography on silica gel (developing solvent: n-hexane/ethyl acetate) and subjected to crystallization from n-hexane/ethyl acetate to obtain 360 mg (yield: 32.8%) of the title compound.

Appearance: colorless crystals. Melting point: 127°–128° C. PMR (δ ppm, CDCl$_3$): 4.23(s,2H), 6.7–7.9(m,14H).

Example 19

Synthesis of 3-(4-phenoxybenzenesulfonyl)-1-phenyl-imidazolidin-2,4-dione (Compound 19):

To a solution of 1.25 g (8.29 mmol) of N-phenylaminoacetic acid in 100 ml of tetrahydrofuran, 2.0 g (8.29 mmol) of 4-phenoxybenzenesulfonyl isocyanate were added at room temperature, and the resultant mixture was stirred for 16 hours. After completion of the reaction, the liquid reaction mixture was cooled to 0° C. and added with 2.09 g (20.7 mmol) of triethylamine and 900 mg (8.29 mmol) of ethyl chloroacetate, followed by stirring at 0° C. for 1 hour. After completion of the reaction, the liquid reaction mixture was added with 40 ml of 1N hydrochloric acid and 60 ml of saturated saline and subjected to extraction with ethyl acetate. After washing the resultant extract with water, it was dried over anhydrous sodium sulfate and then concentrated under reduced pressure. The thus-obtained crude product was purified by column chromatography on silica gel (hexane/ethyl acetate=3:1) and subjected to crystallization from hexane/ethyl acetate, thereby obtaining 310 mg (yield: 9.2%) of the title compound.

Appearance: colorless crystals. Melting point: 157°–157.5° C. PMR (d ppm, CDCl$_3$): 4.32(s,2H), 7.0–8.2 (m,14H).

Example 20

Synthesis of 1-phenyl-3-(3-methoxybenzenesulfonyl)-imidazolidin-2,4-dione (Compound 20 ):

In a similar manner to Example 19, 0.30 g (yield: 3.8%) of the title compound was obtained from 3.39 g (22.5 mmol) of N-phenylaminoacetic acid and 4.78 g (22.5 mmol) of 3-methoxybenzenesulfonyl isocyanate.

Appearance: colorless crystals. Melting point: 201°–201.5° C. PMR (δ ppm, CDCl$_3$): 3.89(s,3H), 4.31(s, 2H), 7.1–7.8(m,9H).

Example 21

Synthesis of 1-phenyl-3-(4-methoxybenzenesulfonyl)-imidazolidin-2,4-dione (Compound 21):

In a similar manner to Example 19, 1.70 g (yield: 35.1%) of the title compound were obtained from 2.10 g (13.9 mmol) of N-phenylaminoacetic acid and 2.95 g (13.9 mmol) of 4-methoxybenzenesulfonyl isocyanate.

Appearance: colorless crystals. Melting point: 210.5°–211° C. PMR (δ ppm, DMSO-d$_6$): 3.86(s,3H), 4.51 (s,2H), 7.1–8.0(m,9H).

Example 22

Synthesis of 3-(3,4-dimethoxybenzenesulfonyl)-1-phenyl-imidazolidin-2,4-dione (Compound 22):

In a similar manner to Example 19, 2.01 g (yield: 38.7%) of the title compound were obtained from 2.09 g (13.8 mmol) of N-phenylaminoacetic acid and 3.35 g (13.8 mmol) of 3,4-dimethoxybenzenesulfonyl isocyanate.

Appearance: colorless crystals. Melting point: 209°–210° C. PMR (δ ppm, DMSO-d$_6$): 3.83(s,3H), 3.87(s,3H), 4.51 (s,2H), 7.1–7.7(m,8H).

Example 23

Synthesis of 3-(4-fluorobenzenesulfonyl)-1-phenyl-imidazolidin-2,4-dione (Compound 23):

In a similar manner to Example 19, 2.41 g (yield: 50.2%) of the title compound were obtained from 2.09 g (13.8 mmol) of N-phenylaminoacetic acid and 2.75 g (13.8 mmol) of 4-fluorobenzenesulfonyl isocyanate.

Appearance: colorless crystals. Melting point: 196.5°–197° C. PMR (δ ppm, DMSO-d$_6$): 4.51(s,2H), 7.1–8.2(m,9H).

Example 24

Synthesis of 3-(4-bromobenzenesulfonyl)-1-phenyl-imidazolidin-2,4-dione (Compound 24):

In a similar manner to Example 19, 3.15 g (yield: 56.5%) of the title compound were obtained from 2.05 g (13.6 mmol) of N-phenylaminoacetic acid and 3.55 g (13.6 mmol) of 4-bromobenzenesulfonyl isocyanate.

Appearance: colorless crystals. Melting point: 190°–191° C. PMR (δ ppm, DMSO-d$_6$): 4.50(s,2H), 7.0–8.0(m,9H).

Example 25

Synthesis of 3-(3-phenoxybenzenesulfonyl)-1-phenyl-imidazolidin-2,4-dione (Compound 25):

In a similar manner to Example 19, 2.04 g (yield: 45.3%) of the title compound were obtained from 1.67 g (11.1 mmol) of N-phenylaminoacetic acid and 2.69 g (11.1 mmol) of 3-phenoxybenzenesulfonyl isocyanate.

Appearance: colorless crystals. Melting point: 150°–151° C.

PMR (δ ppm, DMSO-d$_6$): 4.52(s,2H), 7.1–7.8(m,14H).

Example 26

Synthesis of 3-(4-nitrobenzenesulfonyl)-1-phenyl-imidazolidin-2,4dione (Compound 26):

In a similar manner to Example 19, 0.54 g (yield: 11.6%) of the title compound was obtained from 1.87 g (12.4 mmol) of N-phenylaminoacetic acid and 2.82 g (12.4 mmol) of 4-nitrobenzenesulfonyl isocyanate.

Appearance: colorless crystals. Melting point: 203.5°–204.5° C. PMR (δ ppm, DMSO-d$_6$): 4.52(s,2H), 7.1–8.5(m,9H).

Example 27

Synthesis of 3-(3,4-dimethylbenzenesulfonyl)-1-phenyl-imidazolidin-2,4dione (Compound 27):

In a similar manner to Example 19, 1.93 g (yield: 49.6%) of the title compound were obtained from 1.63 g (10.8 mmol) of N-phenylaminoacetic acid and 2.78 g (10.8 mmol) of 3,4-dimethylbenzenesulfonyl isocyanate.

Appearance: colorless crystals. Melting point: 227°–228° C. PMR (δ ppm, DMSO-d$_6$): 2.32(s,6H), 4.52(s,2H), 7.1–7.8(m,8H).

Example 28

Synthesis of 1-phenyl-3-(4-phenylbenzenesulfonyl)-imidazolidin-2,4dione (Compound 28):

In a similar manner to Example 19, 0.11 g (yield: 28.3%) of the title compound was obtained from 0.15 g (0.99 mmol) of N-phenylaminoacetic acid and 0.26 g (0.99 mmol) of 4-phenylbenzenesulfonyl isocyanate.

Appearance: colorless crystals. Melting point: 222°–224° C. PMR (δ ppm, DMSO-d$_6$): 4.53(s,2H), 7.1–8.2(m,14H).

Example 29

Synthesis of 3-(1,4-benzodioxane-6-sulfonyl)-1-phenyl-imidazolidin-2,4-dione (Compound 29):

In a similar manner to Example 19, 0.33 g (yield: 39.6%) of the title compound was obtained from 0.34 g (2.25 mmol) of N-phenylaminoacetic acid and 0.56 g (2.22 mmol) of 1,4-benzodioxane-6-sulfonyl isocyanate.

Appearance: colorless crystals. Melting point: 225.5°–226° C. PMR (δ ppm, DMSO-d$_6$): 4.3—4.3(m,4H), 4.51(s,2H), 7.1–7.6(m,8H).

Example 30

Synthesis of 3-(4-chlorobenzenesulfonyl)-1-(4-phenoxyphenyl)-imidazolidin-2,4-dione (Compound 30):

In a similar manner to Example 19, 0.53 g (yield: 51.3%) of the title compound was obtained from 0.57 g (2.35 mmol) of N-(4-phenoxyphenyl)aminoacetic acid and 0.60 g (2.34 mmol) of 4-chlorobenzenesulfonyl isocyanate.

Appearance: colorless crystals. Melting point: 179.5°–181° C. PMR (δ ppm, DMSO-d$_6$): 4.50(s,2H), 6.9–8.1(m,13H).

Example 31

Synthesis of 3-(4-chlorobenzenesulfonyl)-1-(2-phenoxyphenyl)-imidazolidin-2,4-dione (Compound 31):

In a similar manner to Example 19, 0.53 g (yield: 51.3%) of the title compound was obtained from 0.57 g (2.35 mmol) of N-(2-phenoxyphenyl)aminoacetic acid and 0.60 g (2.34 mmol) of 4-chlorobenzenesulfonyl isocyanate.

Appearance: colorless crystals. Melting point: 179.5°–181° C. PMR ($\delta$ ppm, DMSO-$d_6$): 4.50(s,2H), 6.9–8.1(m,13H).

Example 32

Synthesis of 3-(3-methoxycarbonylbenzenesulfonyl)-1-phenyl-imidazolidin-2,4-dione (Compound 32):

In a similar manner to Example 19, 0.41 g (yield: 47.4%) of the title compound was obtained from 0.35 g (2.32 mmol) of N-phenylaminoacetic acid and 0.56 g (2.32 mmol) of 3-methoxycarbonylbenzenesulfonyl isocyanate.

Appearance: colorless crystals. Melting point: 170°–171° C. PMR ($\delta$ ppm, DMSO-$d_6$): 3.92(s,3H), 4.51(s,2H), 7.1–8.4(m,8H), 9.28(s,1H)

Example 33

Synthesis of 3-(3-allyloxycarbonylbenzenesulfonyl)-1-phenyl-imidazolidin-2,4-dione (Compound 33):

In a similar manner to Example 19, 2.50 g (yield: 55.7%) of the title compound was obtained from 3.10 g (11.61 mmol) of N-phenylaminoacetic acid and 0.66 g (2.47 mmol) of 3-allyloxycarbonylbenzenesulfonyl isocyanate.

Appearance: colorless crystals. Melting point: 155.5°–156° C. PMR ($\delta$ ppm, DMSO-$d_6$): 4.50(s,2H), 4.8–4.9(d,2H), 5.2–5.5(d,2H), 6.0–6.1(m,1H), 7.1–8.6(m, 9H).

Example 34

Synthesis of 3-(3-carboxybenzenesulfonyl)-1-phenyl-imidazolidin-2,4-dione (Compound 34):

In 10 ml of a 10% solution of formic acid in tetrahydrofuran (THF), were dissolved 400 mg (1.00 mmol) of 3-(3-allyloxycarbonylbenzenesulfonyl)-1-phenyl-imidazolidin-2,4-dione obtained in Example 33. The resultant solution wad deaerated under reduced pressure. To the solution, 50 mg of tetrakis(triphenylphosphine)palladium and 50 mg of triphenylphosphine were added, followed by stirring at room temperature for 2 hours under shielding from the light. After completion of the reaction, the liquid reaction mixture was concentrated under reduced pressure, and crude crystals obtained as residue were collected by filtration, washed with ethyl acetate and then dried, thereby obtaining 350 mg (yield: 97.0%) of the title compound.

Appearance: colorless crystals. Melting point: 231°–232° C. (decomposed). PMR ($\delta$ ppm, DMSO-$d_6$): 4.50(s,2H), 7.1–8.4(m,8H), 8.54(s,1H), 13.68(s,1H).

Example 35

Synthesis of 3-(3-methoxycarbonylbenzenesulfonyl)1-phenyl-imidazolidin-2,4-dione (Compound 35):

In a similar manner to Example 19, 0.28 g (yield: 32.3%) of the title compound was obtained from 0.35 g (2.32 mmol) of N-phenylaminoacetic acid and 0.56 g (2.32 mmol) of 3-methoxycarbonylbenzenesulfonyl isocyanate.

Appearance: colorless crystals. Melting point: 186.5°–187.5° C. PMR ($\delta$ ppm, DMSO-$d_6$): 3.90(s,3H), 4.52(s,2H), 7.1–7.6(m,5H), 8.1–8.3(m,4H).

Example 36

Synthesis of 3-(4-allyloxycarbonylbenzenesulfonyl)1-phenyl-imidazolidin-2,4-dione (Compound 36):

In a similar manner to Example 19, 2.53 g (yield: 76.2%) of the title compound were obtained from 1.25 g (8.28 mmol) of N-phenylaminoacetic acid and 2.22 g (8.29 mmol) of 4-allyloxycarbonylbenzenesulfonyl isocyanate.

Appearance: colorless crystals. Melting point: 139°–140.5° C. PMR ($\delta$ ppm, DMSO-$d_6$): 4.52(s,2H), 4.8–4.9(t,2H), 5.2–5.5(m,2H), 6.0–6.1(m,1H), 7.1–8.3(m, 9H).

Example 37

Synthesis of 3-(4-carboxybenzenesulfonyl)-1-phenyl-imidazolidin-2,4-dione (Compound 37):

In a similar manner to Example 34, 1.10 g (yield: 54.3%) of the title compound were obtained from 2.4 g (5.62 mmol) of 3-(4-allyloxycarbonylbenzenesulfonyl)-1-phenyl-imidazolidin-2,4-dione obtained in Example 36.

Appearance: colorless crystals. Melting point: 230°–233° C. (decomposed). PMR ($\delta$ ppm, DMSO-$d_6$): 4.52(s,2H), 7.1–8.2(m,9H), 13.61(s,1H).

Example 38

Synthesis of 3-(4-methoxycarbonylmethyloxy-benzenesulfonyl)-benzenesulfonyl)-1-phenyl-imidazolidin-2,4-dione (Compound 38):

In a similar manner to Example 19, 0.35 g (yield:42.7%) of the title compound was obtained from 0.31 g (2.05 mmol) of N-phenylaminoacetic acid and 0.55 g (2.04 mmol) of 4-methoxycarbonylmethyloxybenzenesulfonyl isocyanate.

Appearance: colorless crystals. Melting point: 204°–206° C. PMR ($\delta$ ppm, DMSO-$d_6$): 3.70(s,3H), 4.51(s,2H), 4.96 (s,2H), 7.1–8.0(m,9H).

Example 39

Synthesis of 3-(4-allyloxycarbonyloxybenzenesulfonyl)-1-phenyl-imidazolidin-2,4-dione (Compound 39 ):

In a similar manner to Example 19, 3.25 g (yield: 68.3%) of the title compound were obtained from 1.67 g (11.1 mmol) of N-phenylaminoacetic acid and 3.29 g (11.1 mmol) of 4-allyloxycarbonyloxybenzenesulfonyl isocyanate.

Appearance: colorless crystals. Melting point: 165°–167° C. PMR ($\delta$ ppm, DMSO-$d_6$): 4.51(s,2H), 4.6–4.7(m,2H), 5.01(s,1H), 5.2–5.4(m,2H), 5.8–6.0(m,1H), 7.1–8.0(m,9H).

Example 40

Synthesis of 3-(4-carboxymethyloxybenzenesulfonyl)-1-phenyl-imidazolidin-2,4-dione (Compound 40):

In a similar manner to Example 34, 1.75 g (yield: 66.5%) of the title compound were obtained from 2.95 g (6.47 mmol) of 3-(4-allyloxycarbonyloxybenzenesulfonyl)-1-phenyl-imidazolidin-2,4-dione obtained in Example 39.

Appearance: colorless crystals. Melting point: 223.5°–225° C. (decomposed). PMR ($\delta$ ppm, DMSO-$d_6$): 4.51(s,2H), 4.75(s,2H), 7.1–8.0(m,9H).

Example 41

Synthesis of 3-(4-methoxycarbonylmethylbenzenesulfonyl)-1-phenyl-imidazolidin-2,4-dione (Compound 41):

In a similar manner to Example 19, 0.28 g (yield: 33.1%) of the title compound was obtained from 0.33 g (2.19 mmol)

of N-phenylaminoacetic acid and 0.56 g (2.18 mmol) of 4-methoxycarbonylmethylbenzenesulfonyl isocyanate.

Appearance: colorless crystals. Melting point: 204°–206° C. PMR (δ ppm, DMSO-$d_6$): 3.62(s,3H), 3.86(s,2H), 4.53 (s,2H), 7.1–8.1(m,9H).

Example 42

Synthesis of 3-(4-allyloxycarbonyloxybenzenesulfonyl)-1-phenyl-imidazolidin-2,4-dione (Compound 42):

In a similar manner to Example 19, 1.37 g (yield: 56.3%) of the title compound were obtained from 0.89 g (5.89 mmol) of N-phenylaminoacetic acid and 1.65 g (5.88 mmol) of 4-allyloxycarbonylmethylbenzenesulfonyl isocyanate.

Appearance: colorless crystals. Melting point: 152°–154° C. PMR (δ ppm, DMSO-$d_6$): 3.90(s,2H), 4.53(s,2H), 4.4–5.9(m,5H), 7.1–8.1(m,9H).

Example 43

Synthesis of 3-(4-carboxymethyloxybenzenesulfonyl)-1-phenyl-imidazolidin-2,4-dione (Compound 43):

In a similar manner to Example 34, 0.75 g (yield: 76.6%) of the title compound was obtained from 1.17 g (2.65 mmol) of 3-(4-allyloxycarbonylmethylbenzenesulfonyl)-1-phenyl-imidazolidin-2,4-dione obtained in Example 42.

Appearance: colorless crystals. Melting point: 239°–239.5° C. (decomposed). PMR (δ ppm, DMSO-$d_6$): 3.75(s,2H), 4.53(s,2H), 7.1–8.0(m,9H), 12.57(s,1H).

Example 44

Synthesis of 3-(3-methoxycarbonylmethylbenzenesulfonyl)-1-phenyl-imidazolidin-2,4-dione (Compound 44):

In a similar manner to Example 19, 0.23 g (yield: 27.1%) of the title compound was obtained from 0.33 g (2.19 mmol) of N-phenylaminoacetic acid and 0.56 g (2.18 mmol) of 3-methoxycarbonylmethylbenzenesulfonyl isocyanate.

Appearance: colorless crystals. Melting point: 151.5°–152° C. PMR (δ ppm, DMSO-$d_6$): 3.63(s,3H), 3.89 (s,2H), 4.54(s,2H), 7.1–8.0(m,9H).

Example 45

Synthesis of 3-(3-allyloxycarbonylmethylbenzenesulfonyl)-1-phenyl-imidazolidin-2,4-dione (Compound 45):

In a similar manner to Example 19, 0.55 g (yield: 13.6%) of the title compound was obtained from 1.48 g (9.80 mmol) of N-phenylaminoacetic acid and 2.76 g (9.80 mmol) of 3-allyloxycarbonylmethylbenzenesulfonyl isocyanate.

Appearance: colorless crystals. Melting point: 124°–125° C. PMR (δ ppm, DMSO-$d_6$): 3.92(s,2H), 4.54(s,2H), 4.4–6.0(m,5H), 7.1–8.0(m,9H).

Example 46

Synthesis of 3-(3-carboxymethyloxybenzenesulfonyl)-1-phenyl-imidazolidin-2,4-dione (Compound 46):

In a similar manner to Example 34, 80 mg (yield: 22.7%) of the title compound were obtained from 0.43 g (0.97 mmol) of 3-(3-allyloxycarbonylmethylbenzenesulfonyl)-1-phenyl-imidazolidin-2,4-dione obtained in Example 45.

Appearance: colorless crystals. Melting point: 205°–206° C. (decomposed). PMR (δ ppm, DMSO-$d_6$): 3.76(s,2H), 4.54(s,2H), 7.1–7.8(m,7H), 7.96(s,2H), 12.53(s,1H).

Example 47

Synthesis of 3-(3-N-methylpiperazylcarbonylbenzenesulfonyl)-1-phenyl-imidazolidin-2,4-dione (Compound 47):

In 1.0 ml of thionyl chloride, were suspended 200 mg (0.56 mmol) of 3-(3-carboxybenzenesulfonyl)-1-phenyl-imidazolidin-2,4-dione obtained in Example 34, and the suspension was stirred at 80° C. for 2 hours to form an acid chloride. After completion of the reaction, the liquid reaction mixture was concentrated under reduced pressure. The resultant residue was dissolved in 25 ml of THF, and 0.065 ml (0.59 mmol) of N-methylpiperazine was added to the resultant solution while chilling with ice water, followed by stirring for 30 minutes. Colorless crystals deposited in the liquid reaction mixture were collected by filtration, thereby obtaining 140 mg (yield: 52.6%) of the title compound as the hydrochloride.

Appearance: colorless crystals. Melting point: 151°–153° C. PMR (δ ppm, DMSO-$d_6$): 2.76(s,3H), 2.8–3.8(m,8H), 4.52(s,2H), 7.1–8.2(m,9H), 10.9–11.2(s,1H).

Example 48

Synthesis of 3-(4-N-methylpiperazylcarbonylbenzenesulfonyl)-1-phenyl-imidazolidin-2,4-dione (Compound 48):

In a similar manner to Example 47, 230 mg (yield: 86.5%) of the title compound were obtained as the hydrochloride from 0.20 g (0.56 mmol) of 3-(4-carboxybenzenesulfonyl)-1-phenyl-imidazolidin-2,4-dione obtained in Example 37.

Appearance: colorless crystals. Melting point: 212°–214° C. PMR (δ ppm, DMSO-$d_6$): 2.75(s,3H), 2.9–3.8(m,8H), 4.53(s,2H), 7.1–8.2(m,9H), 11.14(s,1H).

Example 49

Synthesis of 3-(4-N-methylpiperazylcarbonyl-methyloxybenzenesulfonyl)-1-phenyl-imidazolidin-2,4-dione (Compound 49):

In a similar manner to Example 47, 140 mg (yield: 53.7%) of the title compound were obtained as the hydrochloride from 0.20 g (0.51 mmol) of 3-(4-carboxy-methyloxybenzenesulfonyl)-1-phenyl-imidazolidin-2,4-dione obtained in Example 40.

Appearance: colorless crystals. Melting point: 150°–154° C. PMR (δ ppm, DMSO-$d_6$): 2.74(s,3H), 2.9–3.5(m,8H), 4.52(s,2H), 5.09(s,2H), 7.1–8.0(m,9H), 9.8–10.5(brs,1H).

Example 50

Synthesis of 3-(4-N-methylpiperazylcarbonyl-methylbenzenesulfonyl)-1-phenyl-imidazolidin-2,4-dione (Compound 50):

In a similar manner to Example 47, 80 mg (yield: 30.3%) of the title compound were obtained as the hydrochloride from 0.20 g (0.53 mmol) of 3-(4-carboxy-methylbenzenesulfonyl)-1-phenyl-imidazolidin-2,4-dione obtained in Example 43.

Appearance: colorless crystals. Melting point: 177°–178° C. PMR (δ ppm, DMSO-$d_6$): 2.79(s,3H), 2.9–3.9(m,8H), 3.53(s,2H), 4.53(s,2H), 7.1–8.3(m,9H), 9.4–9.9(s,1H).

Example 51

Synthesis of 3-(3,4-dichlorobenzenesulfonyl)-1-phenyl-imidazolidin-2,4-dione (Compound 51):

In a similar manner to Example 19, 0.14 g (yield: 5.0%) of the title compound was obtained from 1.06 g (7.02 mmol) of N-phenylaminoacetic acid and 1.65 g (7.02 mmol) of 3,4-dichlorobenzenesulfonyl isocyanate.

Appearance: colorless crystals. Melting point: 217°–218° C. PMR (δ ppm, DMSO-$d_6$): 4.42(s,2H), 7.3–7.6(m,5H), 7.8–8.5(m,3H).

Example 52

Synthesis of 1-(4-acetylaminophenyl)-3-(4-chlorobenzenesulfonyl)-imidazolidin-2,4-dione (Compound 52):

In a similar manner to Example 19, 100 mg (yield: 22.7%) of the title compound were obtained from 0.23 g (1.11 mmol) of N-(4-acetylamino)phenylaminoacetic acid and 0.26 g (1.11 mmol) of 4-chlorobenzenesulfonyl isocyanate.

Appearance: colorless crystals. Melting point: 250°–251° C. PMR (δ ppm, DMSO-$d_6$): 2.06(s,3H), 4.54(s,2H), 7.5–7.7(m,4H), 7.8–8.3(m,4H).

Example 53

Synthesis of 1-(4-t-butoxycarbonylethyl)-3-(4-chlorobenzenesulfonyl)-imidazolidin-2,4-dione (Compound 53):

In a similar manner to Example 19, 1.5 g (yield: 36.7%) of the title compound were obtained from 2.26 g (9.00 mmol) of N-(4-t-butoxycarbonyl)phenylaminoacetic acid and 1.96 g (9.0 mmol) of 4-chlorobenzenesulfonyl isocyanate.

Appearance: colorless crystals. Melting point: 267°–268° C. PMR (δ ppm, DMSO-$d_6$): 1.52(s,9H), 4.52(s,2H), 7.6–8.1(m,8H).

Example 54

Synthesis of 1-(4-carboxyphenyl)-3-(4-chlorobenzenesulfonyl)-imidazolidin-2,4-dione (Compound 54):

In 1.5 ml of trifluoroacetic acid (TFA), were dissolved 120 mg (0.27 mmol) of 1-(4-t-butoxycarbonylphenyl)-3-(4-chlorobenzenesulfonyl)-imidazolidin-2,4-dione obtained in Example 53. The resultant solution was stirred at room temperature for 10 minutes. The liquid reaction mixture was concentrated under reduced pressure and added with diethyl ether. Crystals deposited were collected by filtration to obtain 90 mg (yield: 85.2%) of the title compound.

Appearance: colorless crystals. Melting point: 271°–272° C. PMR (δ ppm, DMSO-$d_6$): 4.51(s,2H), 7.6–8.1(m,8H).

Example 55

Synthesis of 1-(3-butoxycarbonylphenyl)-3-(4-chlorobenzenesulfonyl)-imidazolidin-2,4-dione (Compound 55):

In a similar manner to Example 19, 0.57 g (yield: 9.7%) of the title compound was obtained from 3.26 g (13.0 mmol) of N-(3-t-butoxycarbonyl)phenylaminoacetic acid and 2.80 g (13.0 mmol) of 4-chlorobenzenesulfonyl isocyanate.

Appearance: colorless crystals. Melting point: 167°–168° C. PMR (3 ppm, DMSO-$d_6$): 1.53(s,9H), 4.54(s,2H), 7.5–8.1(m,8H).

Example 56

Synthesis of 1-(3-carboxyphenyl)-3-(4-chlorobenzenesulfonyl)-imidazolidin-2,4-dione (Compound 56):

In a similar manner to Example 54, 160 mg (yield: 74.5%) of the title compound were obtained from 250 mg (0.55 mmol) of 1-(3-t-butoxyphenyl)-3-(4-chlorobenzenesulfonyl)-imidazolidin-2,4-dione obtained in Example 55.

Appearance: colorless crystals. Melting point: 254°–255° C. PMR (3 ppm, DMSO-$d_6$): 4.54(s,2H), 7.5–8.3(m,8H).

Example 57

Synthesis of 1-(2-t-butoxycarbonylphenyl)-3-(4-chlorobenzenesulfonyl)-imidazolidin-2,4-dione (Compound 57):

In a similar manner to Example 19, 0.12 g (yield: 6.8%) of the title compound was obtained from 1.00 g (3.98 mmol) of N-(2-t-butoxycarbonyl)phenylaminoacetic acid and 0.87 g (4.0 mmol) of 4-chlorobenzenesulfonyl isocyanate.

Appearance: colorless crystals. Melting point: 144°–145° C. PMR (3 ppm, DMSO-$d_6$): 1.34(s,9H), 4.52(s,2H), 7.5–8.1(m,8H).

Example 58

Synthesis of 1-(2-carboxyphenyl)-3-(4-chlorobenzenesulfonyl)-imidazolidin-2,4-dione (Compound 58):

In a similar manner to Example 54, 50 mg (quantitative) of the title compound were obtained from 60 mg (0.13 mmol) of 1-(2-t-butoxycarbonylphenyl)-3-(4-chlorobenzene-sulfonyl)-imidazolidin-2,4-dione obtained in Example 57.

Appearance: colorless crystals. Melting point: 208°–209° C. PMR (δ ppm, DMSO-$d_6$): 4.46(s,2H), 7.4–8.3(m,8H).

Example 59

Synthesis of 3-(4-chlorobenzenesulfonyl)-1-(3,4-dimethoxyphenyl)-imidazolidin-2,4-dione (Compound 59):

In a similar manner to Example 19, 0.92 g (yield: 44.8%) of the title compound was obtained from 1.06 g (5.02 mmol) of N-(3,4-dimethoxy)phenylaminoacetic acid and 1.09 g (5.0 mmol) of 4-chlorobenzenesulfonyl isocyanate.

Appearance: colorless crystals. Melting point: 186°–187° C. PMR (δ ppm, DMSO-$d_6$): 3.72(s,3H), 3.73(s,3H), 4.48 (s,2H), 7.0–8.1(m,7H).

Example 60

Synthesis of 3-(3,4-dimethylbenzenesulfonyl)-1-(3,4-dimethoxyphenyl)-imidazolidin-2,4-dione (Compound 60):

In a similar manner to Example 19, 375 mg (yield: 18.1%) of the title compound were obtained from 1.00 g (5.59 mmol) of N-(3,4-dimethyl)phenylaminoacetic acid and 1.25 g (5.57 mmol) of 3,4-dimethylbenzenesulfonyl isocyanate.

Appearance: colorless crystals. Melting point: 165°–166° C. PMR (δ ppm, CD$_3$OD): 2.22(s,3H), 2.25(s,3H), 4.25(s,2H), 7.1–8.0(m,6H).

Example 61

Synthesis of 3-(3,4-dimethylbenzenesulfonyl)-1-(3,4-dimethoxyphenyl)-imidazolidin-2,4-dione (Compound 61):

In a similar manner to Example 19, 754 mg (yield: 33.4%) of the title compound were obtained from 1.00 g (5.59 mmol) of N-(3,4-dimethyl)phenylaminoacetic acid and 1.43 g (5.58 mmol) of 3,4-dimethoxybenzenesulfonyl isocyanate.

Appearance: colorless crystals. Melting point: 195°–197° C. PMR (δ ppm, CDCl$_3$): 2.23(s,3H), 2.25(s,3H), 3.96(s,6H), 4.27(s,2H), 7.0–7.9(m,6H).

Example 62

Synthesis of 3-(3,4-dichlorobenzenesulfonyl)-1-(3,4-dimethoxyphenyl)-imidazolidin-2,4-dione (Compound 62):

In a similar manner to Example 19, 1.06 g (yield: 45.9%) of the title compound were obtained from 1.00 g (5.59 mmol) of N-(3,4-dimethyl)phenylaminoacetic acid and 1.48 g (5.58 mmol) of 3,4-dichlorobenzenesulfonyl isocyanate.

Appearance: colorless crystals. Melting point: 247°–249° C. PMR (δ ppm, CDCl$_3$): 2.23(s,3H), 2.26(s,3H), 4.31(s, 2H), 7.1–8.3(m,6H).

Example 63

Synthesis of 3-(4-chlorobenzenesulfonyl)-1-(3-morpholinocarbonylphenyl)-imidazolidin-2,4-dione (Compound 63):

Two hundred milligrams of (0.51 mmol) of 1-(4-carboxyphenyl)-3-(4-chlorobenzenesulfonyl)-imidazolidin-2,4-dione obtained in Example 54 were treated in a similar manner to Example 47 using morpholine in place of N-methylpiperazine, thereby obtaining 60 mg of the title compound (yield: 25.4%).

Appearance: colorless crystals. Melting point: 248°–253° C. PMR (δ ppm, DMSO-d$_6$): 3.30–3.58(m,4H), 4.53(s,2H), 7.4–8.1(m,8H).

Example 64

Synthesis of 3-(4-chlorobenzenesulfonyl)-1-(3-N-methylpiperazylcarbonylphenyl)-imidazolidin-2,4-dione (Compound 64):

In a similar manner to Example 47, 100 mg (yield: 38.2%) of the title compound were obtained as the hydrochloride from 200 mg (0.51 mmol) of 1-(4-carboxy-phenyl)-3-(4-chlorobenzenesulfonyl)-imidazolidi n-2,4-dione obtained in Example 54.

Appearance: colorless crystals. Melting point: 172°–175° C. PMR (δ ppm, DMSO-d$_6$): 2.76(s,3H), 3.4–3.6(m,8H), 4.55(s,2H), 7.5–8.1(m,8H).

Example 65

Synthesis of 3-(4-allyloxycarbonylbenzenesulfonyl)-1-(3,4-dimethylphenyl)-imidazolidin-2,4-dione (Compound 65):

In a similar manner to Example 19, 36 mg (yield: 3.8%) of the title compound were obtained from 0.40 g (2.23 mmol) of N-(3,4-dimethyl)phenylaminoacetic acid and 629 mg (2.24 mmol) of 4-allyloxycarbonylbenzenesulfonyl isocyanate.

Appearance: colorless crystals. Melting point: 145°–149° C. PMR (δ ppm, CDC13): 2.22(s,3H), 2.25(s,3H), 4.29(s, 2H), 4.86(d,2H), 5.3–6.1(m,3H), 7.1–8.3(m,7H).

Example 66

Synthesis of 3-(4-carboxybenzenesulfonyl)-1-(3,4-dimethylphenyl)-imidazolidin-2,4-dione (Compound 66):

In a similar manner to Example 54, 10 mg (yield: 54.5%) of the title compound were obtained from 20 mg (0.046 mmol) of 3-(4-allyloxycarbonylbenzenesulfonyl)-1-(3,4-dimethylphenyl)-imidazolidin-2,4-dione obtained in Example 65.

Appearance: colorless crystals. Melting point: decomposed at 250° C. PMR (δ ppm, DMSO-d$_6$): 2.18(s,3H), 2.21(s,3H), 4.49(s,2H), 7.1–8.3(m,7H), 13.51(s,1H).

Example 67

Synthesis of 3-(3-allyloxycarbonylbenzenesulfonyl)-1-(3,4-dimethylphenyl)-imidazolidin-2,4-dione (Compound 67):

In a similar manner to Example 19, 219 mg (yield: 22.8%) of the title compound were obtained from 0.40 g (2.23 mmol) of N-(3,4-dimethyl)phenylaminoacetic acid and 629 mg (2.24 mmol) of 3-allyloxycarbonylbenzenesulfonyl isocyanate.

Appearance: colorless crystals. Melting point: 169°–170° C. PMR (δ ppm, CDCl$_3$): 2.22(s,3H), 2.25(s,3H), 4.29(s, 2H), 4.86(d,2H), 5.3–6.1(m,3H), 7.1–8.3(m,7H).

Example 68

Synthesis of 3-(3-carboxybenzenesulfonyl)-1-(3,4-dimethylphenyl)-imidazolidin-2,4-dione (Compound 68):

In a similar manner to Example 54, 85 mg (yield: 46.6%) of the title compound were obtained from 201 mg (0.47 mmol) of 3-(3-allyloxycarbonylbenzenesulfonyl)-1-(3,4-dimethylphenyl)-imidazolidin-2,4-dione obtained in Example 67.

Appearance: colorless crystals. Melting point: decomposed at 250° C. PMR (δ ppm, DMSO-d$_6$): 2.18(s,3H), 2.21(s,3H), 4.48(s,2H), 7.1–8.6(m,7H), 13.62(s,1H).

Example 69

Synthesis of 3-(3-cyanobenzenesulfonyl)-1-phenyl)-imidazolidin-2,4-dione (Compound 69):

In a similar manner to Example 19, 484 mg (yield: 25.9%) of the title compound were obtained from 1.14 g (5.49 mmol) of N-phenylaminoacetic acid and 1.14 g (5.49 mmol) of 3-cyanobenzenesulfonyl isocyanate.

Appearance: colorless crystals. Melting point: 194°–195° C. PMR (δ ppm, DMSO-d$_6$): 4.52(s,2H), 7.1–8.5(m,9H).

Example 70

Synthesis of 3-(1-naphthysulfonyl)-1-(phenyl)-imidazolidin-2,4-dione (Compound 70):

To a solution of 787 mg (4.37 mmol) of ethyl N-phenylaminoacetate in 10 ml of benzene, 1.16 g (88%, 4.37 mmol) of 1-naphthalenesulfonyl isocyanate were added, and the resultant mixture was stirred at room temperature for 3 hours. The liquid reaction mixture was then concentrated under reduced pressure, and the resultant residue was dissolved in a liquid mixture composed of 20 ml of 2N aqueous sodium hydroxide/10 ml of tetrahydrofuran, and the solution was stirred for 1 hour while chilling with ice water. After completion of the reaction, the liquid reaction mixture was neutralized and subjected to extraction with ethyl acetate. The extract was washed with water, dried over anhydrous sodium sulfate, and then concentrated under reduced pressure. The resultant residue was dissolved in 30 ml of tetrahydrofuran, and the solution was cooled to 0° C. and then added with 1.10 g (10.93 mmol) of triethylamine and 522 mg (4.81 mmol) of ethyl chloroacetate, followed by stirring for 1 hour while chilling with ice water. After completion of the reaction, the liquid reaction mixture was added with 20 ml of 1N hydrochloric acid and 30 ml of saturated saline and then subjected to extraction with ethyl acetate. After washing the resultant extract with water, it was dried over anhydrous sodium sulfate and then concentrated under reduced pressure. The thus-obtained crude product was purified by column chromatography on silica gel (hexane/ethyl acetate=3:1) and subjected to crystallization from hexane/ethyl acetate, thereby obtaining 150 mg (0.41 mmol) of the title compound as colorless crystals (yield: 9.4%).

Melting point: 242°–243° C. PMR (δ ppm, DMSO-d$_6$): 4.58(s,2H), 7.1–8.8(m,12H).

Example 71

Synthesis of 3-(2-naphthylsulfonyl)-1-(phenyl)-imidazolidin-2,4-dione (Compound 71):

In a similar manner to Example 70, 470 mg (1.28 mmol; yield: 26.6%) of the title compound were obtained as white crystals from 860 mg (4.83 mmol) of ethyl N-phenylaminoacetate and 1.39 g (81%, 4.83 mmol) of 2-naphthalenesulfonyl isocyanate.

Melting point: 208°–210° C. PMR (δ ppm, DMSO-$d_6$): 4.52(s,2H), 7.1–8.3(m,11H), 8.76(s,1H).

Example 72

Synthesis of 1-(3-chlorophenyl)-3-(2-naphthylsulfonyl) imidazolidin-2,4-dione (Compound 72):

In accordance with the synthesis process (B), 1.0 g (81%, 3.49 mmol) of 2-naphthalenesulfonyl isocyanate was added to a solution of 647 mg (3.49 mmol) of N-3-chlorophenylaminoacetic acid in 50 ml of tetrahydrofuran at room temperature, and the resultant mixture was stirred for 16 hours. After completion of the reaction, the liquid reaction mixture was cooled to 0° C. and added with 881 mg (8.72 mmol) of triethylamine and 417 mg (3.84 mmol) of ethyl chloroacetate, followed by stirring at 0° C. for 1 hour. After completion of the reaction, the liquid reaction mixture was added with 20 ml of 1N hydrochloric acid and 30 ml of saturated saline and subjected to extraction with ethyl acetate. After washing the resultant extract with water, it was dried over anhydrous sodium sulfate and then concentrated under reduced pressure. The thus-obtained crude product was purified by column chromatography on silica gel (hexane/ethyl acetate=3:1) and subjected to crystallization from hexane/ethyl acetate, thereby obtaining 324 mg (0.81 mmol) of the title compound as white crystals (yield: 23.2%).

Melting point: 194°–198° C. PMR (δ ppm, DMSO-$d_6$): 4.29(s,2H), 7.1–8.2(m,10H), 8.79(s,1H).

Example 73

Synthesis of 1-(4-chlorophenyl)-3-(2-naphthylsulfonyl) imidazolidin-2,4-dione (Compound 73):

In a similar manner to Example 72, 500 mg (1.25 mmol; yield: 33.1%) of the title compound were obtained as white crystals from 700 mg (3.77 mmol) of N-4-chlorophenylaminoacetic acid and 1.1 g (81%, 3.77 mmol) of 2-naphthalenesulfonyl isocyanate.

Melting point: 227°–228° C. PMR (δ ppm, DMSO-$d_6$): 4.51(s,2H), 7.4–8.3(m,10H), 8.76(s,1H).

Example 74

Synthesis of 1-(2-chlorophenyl)-3-(2-naphthylsulfonyl) imidazolidin-2,4-dione (Compound 74):

In a similar manner to Example 72, 366 mg (0.91 mmol; yield: 26.1%) of the title compound were obtained as white crystals from 650 mg (3.5 mmol) of N-2-chlorophenylaminoacetic acid and 1.0 g (81%, 3.5 mmol) of 2-naphthalenesulfonyl isocyanate.

Melting point: 155°–159° C. PMR (δ ppm, DMSO-$d_6$): 4.38(s,2H), 7.3–8.2(m,10H), 8.78(s,1H).

Example 75

Synthesis of 1-(3,4-dichlorophenyl)-3-(2-naphthylsulfonyl) imidazolidin-2,4-dione (Compound 75):

In a similar manner to Example 72, 150 mg (0.34 mmol; yield: 9.9%) of the title compound were obtained as white crystals from 770 mg (3.5 mmol) of N-3,4-dichlorophenylaminoacetic acid and 1.0 g (81%, 3.5 mmol) of 2-naphthalenesulfonyl isocyanate.

Melting point: 223°–225° C. PMR (δ ppm, DMSO-$d_6$): 4.27(s,2H), 7.3–8.2(m,9H), 8.79(s,1H).

Example 76

Synthesis of 1-(3,4-dimethylphenyl)-3-(2-naphthylsulfonyl) imidazolidin-2,4-dione (Compound 76):

In a similar manner to Example 70, 290 mg (0.75 mmol; yield: 13.0%) of the title compound were obtained as white crystals from 1.19 g (5.74 mmol) of ethyl N-3,4-dimethylphenylaminoacetate and 1.65 g (81%, 5.74 mmol) of 2-naphthalenesulfonyl isocyanate.

Melting point: 190°–192° C. PMR (δ ppm, DMSO-$d_6$): 2.21(s,3H), 2.23(s,3H), 4.28(s,2H), 7.1–8.2(m,9H), 8.80(s, 1H).

Example 77

Synthesis of 1-(1-naphthyl)-3-(2-naphthylsulfonyl) imidazolidin-2,4-dione (Compound 77):

In a similar manner to Example 70, 120 mg (0.29 mmol; yield: 8.0%) of the title compound were obtained as white crystals from 830 mg (3.62 mmol) of ethyl N-1-naphthylaminoacetate and 1.05 g (81%, 3.62 mmol) of 2-naphthalenesulfonyl isocyanate.

Melting point: 189°–191° C. PMR (δ ppm, DMSO-$d_6$): 4.37(s,2H), 7.3–8.2(m,13H), 8.82(s,1H).

Example 78

Synthesis of 1-(1-phenyl)-3-(1-naphthoyl)-imidazolidin-2,4-dione (Compound 78):

In accordance with the synthesis process (B), 950 mg (5.40 mmol) of 1-phenylimidazolidin-2,4-dione were dissolved in 10 ml of pyridine, and the solution was chilled with ice water. To this solution, 1 g (5.28 mmol) of 1-naphthoyl chloride was added, and the resultant mixture was stirred for 1 hour while chilling with ice water, followed by stirring at room temperature for 5 hours. The liquid reaction mixture was poured into 1N hydrochloric acid, followed by extraction with ethyl acetate. After washing the resultant extract with saturated saline, it was dried over anhydrous sodium sulfate. The solvent was distilled out of the extract, and the resultant residue was purified by column chromatography on silica gel (hexane/ethyl acetate=3:1) and subjected to crystallization from hexane/ethyl acetate, thereby obtaining 270 mg (0.84 mmol) of the title compound as white crystals (yield: 15.5%).

Melting point: 192°–196° C. PMR (δ ppm, DMSO-$d_6$): 4.64(s,2H), 7.1–8.5(m,12H).

Example 79

Synthesis of 1-(1-phenyl)-3-(2-naphthoyl)-imidazolidin-2,4-dione (Compound 79):

In a similar manner to Example 78, 150 mg (0.46 mmol; yield: 8.6%) of the title compound were obtained as white crystals from 950 mg (5.40 mmol) of 1-phenylimidazolidin-2,4-dione and 1 g (5.28 mmol) of 2-naphthoyl chloride.

Melting point: 217°–219° C. PMR (δ ppm, DMSO-$d_6$): 4.69(s,2H), 7.1–8.2(m,11H), 8.77(s,1H).

Example 80

Synthesis of 3-(4-chlorobenzenesulfonyl)-1-(3-quinolyl)-imidazolidin-2,4-dione (Compound 80):

In a similar manner to Example 19, 410 mg (yield: 46.8%) of the title compound were obtained from 0.44 g (2.18 mmol) of N-(3-quinolyl)aminoacetic acid and 0.48 g (2.20 mmol) of 4-chlorobenzenesulfonyl isocyanate.

Appearance: colorless crystals. Melting point: 237°–238° C. PMR (δ ppm, DMSO-$d_6$): 4.71(s,2H), 7.6–8.3(m,8H), 8.49(m,1H), 9.29(m,1H).

Example 81

Synthesis of 3-(2-naphthylsulfonyl)-1-(3-quinolyl)-imidazolidin-2,4-dione (Compound 81):

In a similar manner to Example 19, 120 mg (yield: 13.8%) of the title compound were obtained from 0.44 g (2.18 mmol) of N-(3-quinolyl)aminoacetic acid and 0.77 g (2.20 mmol) of 2-naphthylsulfonyl isocyanate.

Appearance: colorless crystals. Melting point: 225°–226° C. PMR (δ ppm, DMSO-$d_6$): 4.73(s,2H), 7.6–8.5(m,10H), 8.89(m, 1H), 9.28(m,1H).

Example 82

Synthesis of 3-(4-chlorobenzenesulfonyl)-1-(2-pyridyl)-imidazolidin-2,4-dione (Compound 82):

In a similar manner to Example 19, 70 mg (yield: 4.5%) of the title compound were obtained from 0.68 g (4.47 mmol) of N-(2-pyridyl)aminoacetic acid and 0.98 g (4.50 mmol) of 4-chlorobenzenesulfonyl isocyanate.

Appearance: colorless crystals. Melting point: 211°–212° C. PMR (δ ppm, DMSO-$d_6$): 4.53(s,2H), 7.25(m,1H), 7.8–8.2(m,6H), 8.43(m,1H).

Example 83

Synthesis of 1-(5-chloropyridin-2-yl)-3-(4-chlorobenzenesulfonyl)-imidazolidin-2,4-dione (Compound 83):

In a similar manner to Example 19, 260 mg (yield: 31.7%) of the title compound were obtained from 0.37 g (1.98 mmol) of N-(5-chloropyridin-2-yl)aminoacetic acid and 0.43 g (1.98 mmol) of 4-chlorobenzenesulfonyl isocyanate.

Appearance: colorless crystals. Melting point: 237°–238° C. (decomposed). PMR (δ ppm, DMSO-$d_6$): 4.35(s,2H), 7.1–8.3(m,7H).

Example 84

Synthesis of 3-(4-chlorobenzenesulfonyl)-1-(2-pyrimidyl)-imidazolidin-2,4-dione (Compound 84):

In a similar manner to Example 19, 700 mg (yield: 65.7%) of the title compound were obtained from 0.46 g (3.01 mmol) of N-(2-pyrimidyl)aminoacetic acid and 0.66 g (3.03 mmol) of 4-chlorobenzenesulfonyl isocyanate.

Appearance: colorless crystals. Melting point: not lower than 250° C. (decomposed). PMR (δ ppm, DMSO-$d_6$): 4.52(s,2H), 7.2–8.8(m,7H).

Test Example 1

Determination of Inhibitory Activity Against Chymase

Human cardiac chymase was purified according to the process of Urata et al. (see the literature described above), and the inhibitory activities of the hydantoin compounds according to the present invention against the chymase were determined in the following manner. Namely, 10 μl of the purified chymase and 5 μl of a solution of a sample to be tested in dimethyl sulfoxide (hereinafter abbreviated as "DMSO") were added to 10 μl of a 20 mM Tris-hydrochloric acid buffer (pH 7.5) containing 2M KCl, and the resultant mixture was preincubated at 37° C. for 10 minutes and then added with 25 μl of a 1 mM solution of Ang I, followed by incubation at 37° C. for 30 minutes. Then, 50 μl of 30% acetic acid were added to stop the enzyme reaction. On the other hand, 5 μl of DMSO were added in place of the solution of the test sample to similarly conduct a reaction as a blank test.

After completion of the reaction, each liquid reaction mixture was subjected to high performance liquid chromatography on Develosil ODS-5 (product of Nomura Kagaku, 4.6 mm across×150 mm long) to develop it at a linear concentration gradient that the concentration of acetonitrile in 0.05% trifluoroacetic acid (hereinafter abbreviated as "TFA") is increased from 0% to 60% in 10 minutes at a flow rate of 2.0 ml/min. Monitoring was performed by the absorbance measurements at 210 nm. Peaks were identified by comparison with standard solutions of Ang I and Ang II. The areas of the peaks were determined by an integrator to quantitate Ang I and Ang II, thereby calculating chymase activity. The inhibitory activity against chymase was determined by calculating an inhibition rate, median inhibitory concentration ($IC_{50}$) on the basis of the value in the blank test.

All the imidazolidine derivatives according to the present invention strongly inhibit the human chymase at concentrations of 100 μM. With respect to typical compounds thereof, the $IC_{50}$ values are shown in Table 1.

Test Example 2

Determination of Inhibitory Activity Against Cathepsin G

To a 20 mM Tris-hydrochloric acid buffer (pH 7.5) containing 2M KCl, were added 20 μl of a solution with cathepsin G (product of Calbiochem Co.) derived from human neutrophil dissolved at a concentration of 2 μg/ml in the same buffer, and 5 μl of a DMSO solution of a sample to be tested, and the resultant mixture was preincubated at 37° C. for 10 minutes and then added with 25 μl of a 1 mM solution of Ang I, followed by incubation at 37° C. for 30 minutes. Then, 50 μl of 30% acetic acid were added to stop the enzyme reaction. On the other hand, 5 μl of DMSO were added in place of the solution of the test sample to similarly conduct a reaction as a blank test. After completion of the reaction, each liquid reaction mixture was treated by high performance liquid chromatography in the same manner as in Test Example 1 to quantitate Ang I and Ang II, thereby calculating cathepsin G activity. The inhibitory activity against cathepsin G was determined by calculating an inhibition rate, median inhibitory concentration ($IC_{50}$) on the basis of the value in the blank test. The results thereof are shown in Table 1.

Test Example 3

Determination of Inhibitory Activity Against Chymotrypsin

To 12 μl of a 20 mM Tris-hydrochloric acid buffer (pH 7.5) containing 2M KCl, were added 8 μl of a solution with bovine pancreas α-chymotrypsin (product of Sigma Chemical Co., TypeII) dissolved at a concentration of 8 μg/ml in a 20 mM aqueous solution of $CaCl_2$ containing 1 mM HCl, and 5 μl of a DMSO solution of a sample to be tested, and the resultant mixture was preincubated at 37° C. for 10 minutes and then added with 25 μl of a 1 mM solution of Ang I, followed by incubation at 37° C. for 15 minutes. Then, 50 μl of 30% acetic acid were added to stop the enzyme reaction. On the other hand, 5 μl of DMSO were added in place of the solution of the test sample to similarly conduct a reaction as a blank test. After completion of the reaction, each liquid reaction mixture was treated by high performance liquid chromatography in the same manner as in Test Example 1 to quantitate Ang I and Ang II, thereby calculating chymotripsin activity. The inhibitory activity against chymotrypsin was determined by calculating an inhibition rate, median inhibitory concentration ($IC_{50}$) on the basis of the value in the blank test. The results thereof are shown in Table 1.

TABLE 1

Inhibitory activities against enzymes ($IC_{50}$, μM)

| Compound No. | Chymase | Cathepsin | Chymotrypsin |
|---|---|---|---|
| 1 | 0.30 | 1.5 | 0.5 |
| 5 | 2.6 | 4.5 | 7.0 |
| 10 | 3.7 | 0.96 | 3.5 |
| 15 | 14.0 | 3.2 | 6.9 |
| 20 | 0.58 | 8.0 | 3.7 |
| 25 | 0.80 | 3.3 | 1.4 |
| 30 | 28.0 | 4.8 | 39.0 |
| 35 | 0.029 | 0.34 | 1.8 |
| 40 | 10.0 | 7.0 | 34.0 |
| 45 | 0.45 | 4.5 | 3.5 |
| 50 | 0.85 | 11.0 | 5.2 |
| 55 | 15.0 | 9.8 | 70.0 |
| 60 | 0.06 | 1.7 | 33.6%* |
| 65 | 0.027 | 1.9 | 8.5 |
| 70 | 0.55 | 1.8 | 1.6 |
| 75 | 0.047 | 0.52 | 2.4 |
| 80 | 0.17 | 19.0 | 90.0 |

*Expressed by inhibition % at 100 μM.

Preparation Example 1

Preparation of Tables:

One hundred grams of Compound (1), 22.5 g of microcrystalline cellulose and 2.5 g of magnesium stearate were mixed, and this mixture was tableted by a single tablet machine, thereby preparing tablets 9 mm in diameter and 250 mg in weight, which each contain 200 mg of Compound (1).

Preparation Example 2

Preparation of Granules:

Thirty grams of Compound (1), 265 g of lactose and 5 g of magnesium stearate were thoroughly mixed, and the mixture was compression-molded. The resultant molding was then ground or granulated and screened, thereby obtaining good granules containing 10% of Compound (1) and having a size of 20–50 mesh.

Preparation Example 3

Preparation of Rectal Suppository:

Witepsol H-15 (product of Dynamit Nobel Co.) was heated and melted, and Compound (6) was added to the melt to give a concentration of 12.5 mg/ml. The mixture was uniformly kneaded and then charged into molds for rectal suppository in an amount of 2 ml per mold. The thus-obtained moldings were cooled to obtain rectal suppositories each containing 25 mg of Compound (6).

Industrial Applicability

According to the present invention, there can be provided a novel imidazolidine derivative, a chymase inhibitor comprising the same as an active ingredient and a medicine comprising the same as an active ingredient, typified by a prophylactic and therapeutic agent for a disease of the cardiac or circulatory system, which is caused by the abnormal acceleration of production of Ang II. In the human, at least two pathways, in which Ang I is converted to Ang II, exist. One is a pathway in which ACE participates, and the other is a pathway in which chymase participates. Accordingly, the inhibition of chymase permits the prophylaxis of and treatment for various diseases of the cardiac or circulatory system, which are caused by the abnormal acceleration of production of Ang II, even in a region in which any ACE inhibitor exhibits no effect.

We claim:

1. An imidazolidine derivative represented by the following formula (1)

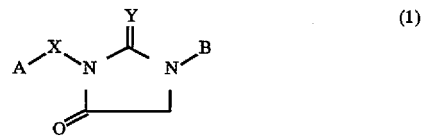

wherein A and B are identical with or different from each other and mean individually an unsubstituted aromatic hydrocarbon group, an aromatic hydrocarbon groups substituted by 1–3 substituents selected from the group consisting of halogen atoms, alkyl groups having 1–4 carbon atoms, alkoxy groups having 1–4 carbon atom, alkylenedioxy groups having 1–4 carbon atoms, a phenoxy group, a nitro group, a cyano group, a phenyl group, alkanoylamino groups having 2–5 carbon atoms, a carboxyl group, a carboxyl group esterified with an alkyl or alkenyl group having 1–4 carbon atoms, carboxyalkyl groups, carboxyalkyl groups esterified with an alkyl or alkenyl group having 1–4 carbon atoms, carboxyalkyloxy groups, carboxyalkyloxy groups esterified with an alkyl or alkenyl group having 1–4 carbon atoms, N-alkylpiperazinylcarbonyl groups, N-alkylpiperazinylcarbonylalkyl groups, N-alkylpiperazinylcarbonylalkyloxy groups, and a morpholinicarbonyl group;

X denotes a sulfonyl or carbonyl group; and

Y stands for an oxygen or sulfur atom, with the proviso that when A and B are identical they are not unsubstituted phenyl when X is a carbonyl group, and when A and B are different from each other, A is not unsubstituted phenyl and chloro-substituted phenyl when B is dimethyl substituted phenyl, Y is a sulfur atom and X is a carbonyl group, and B is not chlorosubstituted phenyl when A is dichloro-substituted phenyl, Y is an oxygen atom and X is a carbonyl group.

2. A medicinal composition comprising an imidazolidine derivative represented by the following formula (1)

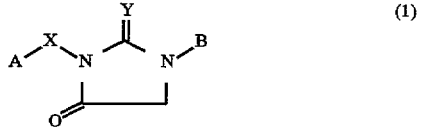

wherein A and B are identical with or different from each other and mean individually an unsubstituted aromatic hydrocarbon group, an aromatic hydrocarbon group substituted by 1–3 substituents selected from the group consisting of halogen atoms, alkyl groups having 1–4 carbon atoms, alkoxy groups having 1–4 carbon atoms, alkylenedioxy groups having 1–4 carbon atoms, a phenoxy group, a nitro group, a cyano group, a phenyl group, alkanoylamino groups having 2–5 carbon atoms, a carboxyl group, a carboxyl group esterified with an alkyl or alkenyl group having 1–4 carbon atoms, carboxyalkyl groups, carboxyalkyl groups esterified with an alkyl or alkenyl group having 1–4 carbon atoms, carboxyalkyloxy groups, carboxyalkyloxy groups esterified with an alkyl or alkenyl group having 1–4 carbon atoms, N-alkylpiperazinylcarbonyl groups, N-alkylpiperazinylcarbonylalkyl groups, N-alkylpiperazinylcarbonylalkyloxy groups, and a morpholinicarbonyl group;

X denotes a sulfonyl or carbonyl group; and

Y stands for an oxygen or sulfur atom and a pharmaceutically permissible carrier.

3. A method of preventing and treating a disease of the heart or circulatory system, which is caused by the abnormal acceleration of production of angiotensin II, comprising administering to a patient an effective amount of an imidazolidine derivative represented by the following formula (1)

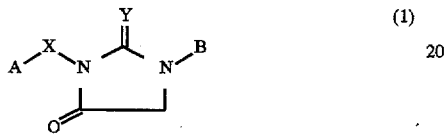 (1)

wherein A and B are identical with or different from each other and mean individually an unsubstituted aromatic hydrocarbon group, an aromatic hydrocarbon group substituted by 1–3 substituents selected from the group consisting of halogen atoms, alkyl groups having 1–4 carbon atoms, alkoxy groups having 1–4 carbon atoms, alkylenedioxy groups having 1–4 carbon atoms, a phenoxy group, a nitro group, a cyano group, a phenyl group, alkanoylamino groups having 2–5 carbon atoms, a carboxyl group, a carboxyl group esterified with an alkyl or alkenyl group having 1–4 carbon atoms, carboxyalkyl groups, carboxyalkyl groups esterified with an alkyl or alkenyl group having 1–4 carbon atoms, carboxyalkyloxy groups, carboxyalkyloxy groups esterified with an alkyl or alkenyl group having 1–4 carbon atoms, N-alkylpiperazinylcarbonyl groups, N-alkylpiperazinylcarbonylalkyl groups, N-alkylpiperazinylcarbonylalkyloxy groups, and a morpholinicarbonyl group;

X denotes a sulfonyl or carbonyl group; and

Y stands for an oxygen or sulfur atom.

4. The method of claim 3, wherein said disease of the heart or circulatory system is selected from the group consisting of heart failure, cardiac hypertrophy, congestive cardiopathy, hypertension, arteriosclerosis, peripheral circulatory failure, vascular restenosis after the operation of percutaneous transluminal coronary angioplasty, and diabetic and nondiabetic nephropathy.

5. A method of inhibiting chymase, comprising contacting chymase with an inhibitory effective amount of an imidazolidine derivative represented by the following formula (1)

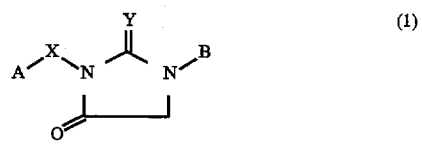 (1)

wherein A and B are identical with or different form each other and mean individually an unsubstituted aromatic hydrocarbon group, an aromatic hydrocarbon group substituted by 1–3 substituents selected from the group consisting of halogen atoms, alkyl groups having 1–4 carbon atoms, alkoxy groups having 1–4 carbon atoms, alkylenedioxy groups having 1–4 carbon atoms, a phenoxy group, a nitro group, a cyano group, a phenyl group, alkanoylamino groups having 2–5 carbon atoms, a carboxyl group, a carboxyl group esterified with an alkyl or alkenyl group having 1–4 carbon atoms, carboxyalkyl groups, carboxyalkyl groups esterified with an alkyl or alkenyl group having 1–4 carbon atoms, carboxyalkoxy groups, carboxyalkyloxy groups esterified with an alkyl or alkenyl group having 1–4 carbon atoms, N-alkylpiperazinylcarbonyl groups, N-alkylpiperazinylcarbonylalkyl groups, N-alkylpiperazinylcarbonylalkyloxy groups, and a morpholinicarbonyl group;

X denotes a sulfonyl or carbonyl group; and

Y stands for an oxygen or sulfur atom.

* * * * *

UNITED STATES PATENT AND TRADEMARK OFFICE
CERTIFICATE OF CORRECTION

PATENT NO. : 5,691,335
DATED : November 25, 1997
INVENTOR(S) : Harukazu FUKAMI, et al.

It is certified that error appears in the above-identified patent and that said Letters Patent is hereby corrected as shown below:

On the title page, item [75], the 5th, 6th, and 7th inventors' names are incorrect, they should be:

[75]

--Masayuki Saitoh--
--Hiroshi Shibata--
--Yoshinobu Kiso--

Signed and Sealed this

Third Day of March, 1998

Attest:

Attesting Officer

BRUCE LEHMAN

Commissioner of Patents and Trademarks